US011093883B2

United States Patent
Zhou et al.

(12) United States Patent
(10) Patent No.: US 11,093,883 B2
(45) Date of Patent: Aug. 17, 2021

(54) APPARATUS, METHOD, AND COMPUTER-READABLE MEDIUM FOR DETERMINING A DRUG FOR MANUFACTURE

(71) Applicant: CAMELOT UK BIDCO LIMITED, London (GB)

(72) Inventors: Xiaodong Zhou, San Francisco, CA (US); ShengLei Cao, San Francisco, CA (US); Matthew Edward Sparrowhawk, London (GB); Laura Vitez, San Francisco, CA (US); Romeo Radman, London (GB); Karthik Subramanian, London (GB); Michael Collingsworth, London (GB); Jean-Sebastien Brien, San Francisco, CA (US)

(73) Assignee: CAMELOT UK BIDCO LIMITED, London (GB)

(*) Notice: Subject to any disclaimer, the term of this patent is extended or adjusted under 35 U.S.C. 154(b) by 273 days.

(21) Appl. No.: 16/104,790

(22) Filed: Aug. 17, 2018

(65) Prior Publication Data
US 2020/0042923 A1    Feb. 6, 2020

Related U.S. Application Data

(60) Provisional application No. 62/714,446, filed on Aug. 3, 2018.

(51) Int. Cl.
*G06Q 10/06* (2012.01)
*G06Q 50/04* (2012.01)
(Continued)

(52) U.S. Cl.
CPC ..... *G06Q 10/06375* (2013.01); *G06Q 10/067* (2013.01); *G06Q 50/04* (2013.01);
(Continued)

(58) Field of Classification Search
CPC ............ G06Q 10/06375; G06Q 50/04; G06Q 10/067; G16H 10/20; G16H 20/10; G16H 50/70; G16H 50/00
See application file for complete search history.

(56) References Cited

U.S. PATENT DOCUMENTS

| 2003/0059837 A1 | 3/2003 | Levinson | |
| 2003/0088365 A1* | 5/2003 | Becker | G16H 10/20 702/19 |

(Continued)

FOREIGN PATENT DOCUMENTS

| WO | WO-03106698 A1 * | 12/2003 | ............ G16C 20/10 |

OTHER PUBLICATIONS

Singh, Assessing the Long-Term Clinical Effectiveness of Inhaled and Anti-Inflammatory Therapies for Lung Disease in Cystic Fibrosis, Aug. 2014, ProQuest, pp. 1-123. (Year: 2014).*

(Continued)

*Primary Examiner* — Christopher L Gilligan
(74) *Attorney, Agent, or Firm* — Oblon, McClelland, Maier & Neustadt, L.L.P.

(57) ABSTRACT

An apparatus, method, and computer readable medium for determination of a drug for manufacture. The apparatus includes processing circuitry configured to receive input data related to one or more drug programs, acquire data from a database, generate one or more models based upon the acquired data from the database, determine, from the one or more models, one or more outputs related to the chronological event, select, based upon the determined one or more outputs, one of the one or more drug programs for manufacture, and transmit, to the manufacturing device via the network, manufacturing information related to the manufacture of the selected one of the one or more drug programs.

15 Claims, 14 Drawing Sheets

(51) Int. Cl.
    G16H 10/20        (2018.01)
    G16H 50/70        (2018.01)
    G16H 50/00        (2018.01)
(52) U.S. Cl.
    CPC ............. *G16H 10/20* (2018.01); *G16H 50/00*
                     (2018.01); *G16H 50/70* (2018.01)

(56) References Cited

U.S. PATENT DOCUMENTS

| | | | | |
|---|---|---|---|---|
| 2006/0161354 | A1* | 7/2006 | Mandema | G16H 50/50 702/19 |
| 2006/0224421 | A1 | 10/2006 | St. Ores et al. | |
| 2008/0086337 | A1* | 4/2008 | Soon-Shiong | G06Q 50/24 705/3 |
| 2012/0041778 | A1 | 2/2012 | Kraft | |
| 2013/0060771 | A1 | 3/2013 | Ho et al. | |
| 2013/0185096 | A1* | 7/2013 | Giusti | G16H 20/40 705/3 |
| 2014/0195170 | A1* | 7/2014 | Avinash | G16C 20/70 702/19 |
| 2015/0363559 | A1 | 12/2015 | Jackson | |
| 2019/0102670 | A1* | 4/2019 | Ceulemans | G06N 3/084 |

OTHER PUBLICATIONS

Alessandra Ferrario, "Access to cancer medicines in Europe: An analysis of existing challenges and countries' responses", London School of Economics and Political Science, Dec. 2016, pp. 1-265.
Karen Kesler, et al., "4 Types of Dose Finding Studies Used in Phase II Clinical Trials", Rho, Mar. 11, 2013, pp. 1-2.
Pierre Biscaye, et al., "Review of Literature on Factors Affecting Private Sector Investment in Global Health R&D", Evans School Policy Analysis and Research, Dec. 5, 2017, pp. 1-83.
"22 Case Studies Where Phase 2 and Phase 3 Trials had Divergent Results", U.S. Food & Drug Administration, Jan. 2017, pp. 1-44.
Chi Heem Wong, et al., "Estimation of clinical trial success rates and related parameters", Biostatistics, vol. 00, No. 00, 2018, pp. 1-47.
Christopher P. Adams, et al., "Estimating the Cost of New Drug Development: Is It Really $802 Million?" Health Affairs, vol. 25, No. 2, Mar./ Apr. 2006, pp. 420-428.
Rosa M. Abrantes-Metz, et al., "Pharmaceutical Development Phases: a Duration Analysis", Bureau of Economics, Working Paper No. 274, Oct. 2004, pp. 1-29.
Anastassios D. Retzios, "Why Do So Many Phase 3 Clinical Trials Fail?: Part 1: The Effect of Deficient Phase 2 Trials in Therapeutic Areas with High Failure Rates in Phase 3 Studies", Bay Clinical R&D Services, Jan. 31, 2010, pp. 1-46.
Robert Kneller, et al., "The importance of new companies for drug discovery: origins of a decade of new drugs", Nature Reviews: Drug Discovery, vol. 9, Nov. 2010, pp. 867-882.
Christopher Horvath, et al., "Comparison of Preclinical Development Programs for Small Molecules (Drug/Pharmaceuticals) and Large Molecules (Biologics/Biopharmaceuticals): Studies, Timing, Materials, and Costs", Pharmaceutical Sciences Encyclopedia: Drug Discovery, Development, and Manufacturing, 2010, pp. 1-36.
Steven M. Paul, et al., "How to improve R&D productivity: the pharmaceutical industry's grand challenge", Nature Reviews: Drug Discovery, vol. 9, Mar. 2010, pp. 203-214.
Jayson L. Parker, et al., "The Success Rate of New Drug Development in Clinical Trials: Crohn's Disease", J Pharm Pharmaceut Sci, vol. 13, No. 2, 2010, pp. 191-197.
Michael Ringel, et al., "Does size matter in R&D productivity? If not, what does?", Nature Reviews: Drug Discovery, vol. 12, Dec. 2013, pp. 901-902.
Lee Y. Hu, et al., "Essays on Market Competition", University of Georgia, 2011, pp. 1-132.

Eliana Barrenho, et al., "The determinants of attrition in drug development: a duration analysis", Imperial College London Business School, Oct. 2013, pp. 1-47.
Ulrik Schulze, et al., "R&D productivity: on the comeback trail", Nature Reviews Drug Discovery, Apr. 22, 2014, pp. 1-4.
David Cook, et al., "Lessons learned from the fate of AstraZeneca's drug pipeline: a five-dimensional framework", Nature Reviews: Drug Discovery, vol. 13, Jun. 2014, pp. 419-431.
Alvaro Arjona, et al., "Clinical Trial Termination at a Glance: Prevalence and Causes", Life Sciences Connect, Jun. 23, 2014, pp. 1-5.
"NCE Investigational New Drug Program Timeline" Charles River, 2015, pp. 1-2.
Aylin Sertkaya, et al., "Analytical Framework for Examining the Value of Antibacterial Products", U.S. Department of Health and Human Services, Assistant Secretary of Planning and Evaluation, Apr. 15, 2014, pp. 1-107.
"2015 CMR International Pharmaceutical R&D Executive Summary" Thomson Reuters, Aug. 2015, pp. 1-7.
Katarzyna Smietana, et al., "Improving R&D productivity", Nature Reviews: Drug Discovery, vol. 14, Jul. 2015, pages.
Peter Lurie, et al., "Comparison of content of FDA letters not approving applications for new drugs and associated public announcements from sponsors: cross sectional study", BMJ, 2015, 1-8.
Lisette Pregelj, et al., "Changes in clinical trial length", Nature Reviews: Drug Discovery, vol. 14, May 2015, pp. 307-308.
Katarzyna Smietana, et al., "Trends in clinical success rates", Nature Reviews: Drug Discovery, vol. 15, 2016, pp. 379-380.
Philippa Crane, et al., "The Uppers and Downers of Drug Development: Why do some drug projects succeed in development while others fail? An exploration into the conditions associated with the success and failure of UK rare cancer drug projects", University of Sussex, Sep. 2015, pp. 1-337.
BW Morrison, "Biotechnology and Translational Medicine", Clinical and Translational Science, Mar. 30, 2016, pp. 1-3.
Paul Morgan, et al., "Can the flow of medicines be improved? Fundamental pharmacokinetic and pharmacological principles toward improving Phase II survival", Drug Discovery Today, vol. 17, Issues 9-10, May 2012, pp. 419-424.
Min Ding, et al., "Innovation and Marketing in the Pharmaceutical Industry: Emerging Practices, Research, and Policies", International Series in Quantitative Marketing 20, 2014, pp. 83-117.
"22 Case Studies Where Phase 2 and Phase 3 Trials had Divergent Results", U.S. Food & Drug Administration, Jan. 2017, pp. 1-43.
Vitor Kamada, "Innovation in the Biopharmaceutical Industry", Georgia Institute of Technology, Aug. 2017, pp. 1-116.
Joseph A. Dimasi, et al., "The Impact of Collaborative and Risk-Sharing Innovation Approaches on Clinical and Regulatory Cycle Times", Therapeutic Innovation & Regulatory Science, vol. 48, No. 4, 2014, pp. 482-487.
Percy H. Carter, et al., "Investigating investment in biopharmaceutical R&D", Nature Reviews: Drug Discovery, vol. 15, Oct. 2016, pp. 673-674.
"Streamlined Development Process for Certain New Drug Applications Is Not Facilitating Shorter Approval Times", Tufts Center for the Study of Drug Development, Mar. 8, 2017, pp. 1-2.
Joseph A. Dimasi, et al., "Innovation in the pharmaceutical industry: New estimates of R&D costs", Journal of Health Economics, vol. 47, 2016, pp. 20-33.
Joseph A. Dimasi, et al., "The price of innovation: new estimates of drug development costs", Journal of Health Economics, vol. 22, 2003, pp. 151-185.
John A. Vernon, et al., "Drug Development Costs When Financial Risk Is Measured Using the FAMA-French Three-Factor Model", Health Economics, vol. 19, 2010, pp. 1002-1005.
Joseph A. Dimasi, et al., "The Cost of Biopharmaceutical R&D: Is Biotech Different?", Managerial and Decision Economics, vol. 28, 2007, pp. 469-479.
JA Dimasi, et al., "Trends in Risks Associated With New Drug Development: Success Rates for Investigational Drugs", Clinical Pharmacological & Therapeutics, vol. 87, No. 3, Mar. 2010, pp. 272-277.

(56) References Cited

OTHER PUBLICATIONS

Joseph A. Dimasi, et al., "Competitiveness in follow-on drug R&D: a race or imitation?", Nature Reviews: Drug Discovery, vol. 10, Jan. 2011, pp. 23-27.
"Outlook 2012", Tufts Center for the Study of Drug Development, 2012, pp. 1-16.
"Outlook 2013", Tufts Center for the Study of Drug Development, 2013, pp. 1-16.
JA Dimasi, et al., "Clinical Approval Success Rates for Investigational Cancer Drugs", Clinical Pharmacology & Therapeutics, vol. 94, No. 3, Sep. 2013, pp. 329-335.
"A New Tool for Predicting Marketing Approval of Oncology Drugs", Tufts Center for the Study of Drug Development and Janssen Research & Development, 2013, pp. 1-9.
Joseph A. Dimasi, et al., "Pharmaceutical R&D Performance by Firm Size: Approval Success Rates and Economic Returns", American Journal of Therapeutics, vol. 21, 2014, pp. 26-34.
RP Evans, et al., "The Biotechnology Innovation Machine: A Source of Intelligent Biopharmaceuticals for the Pharma Industry—Mapping Biotechnology's Success", Clinical Pharmacology & Therapeutics, vol. 95, No. 5, May 2014, pp. 528-532.
Joseph A. Dimassi, "Innovating by Developing New Uses of Already-Approved Drugs: Trends in the Marketing Approval of Supplemental Indications", Clinical Therapeutics, vol. 35, Issue 6, Jun. 2013, pp. 808-818.
Joseph A. Dimasi, et al., "Innovation in the Pharmaceutical Industry: New Estimates of R&D Costs", Tufts Center for the Study of Drug Development, Nov. 18, 2014, pp. 1-30.
Asher Mullard, "News in Brief", Nature Reviews: Drug Discovery, vol. 15, Jul. 2016, p. 447.
Ellen Moore, et al., "Oncology Scorecard—Who's Succeeding at Cancer Drug Development", Pharma Intelligence, 2016, pp. 1-12, https://www.slideshare.net/Informa_Healthcare/discover-who-is-succeeding-at-cancer-drug-development.
"High Impact Catalysts: Early 2017 Outlook Report", Biomedtracker and Meddevice Tracker, 2017, p. 1.
"2017 ASCO Weekend Update", Biomedtracker, Jun. 2017, pp. 1-5, 18-21.
"Pharma Consulting", Informa UK Ltd, Feb. 2018, pp. 1-8.
Michael Hay, et al., "BIO/BioMedTracker Clinical Trial Success Rates Study", BIO CEO & Investor Conference, Feb. 15, 2011, pp. 1-12.
Michael Hay, et al., "BioMedTracker Clinical Development Success Rates for Investigational Drugs", Pharma CI 2012, pp. 1-29.
Michael Hay, et al., "Clinical development success rates for investigational drugs", Nature Biotechnology, vol. 32, No. 1, Jan. 2014, pp. 40-51.
Biomedtracker brochure, Pharma intelligence: informa, pp. 1-16, pharmaintelligence.informa.com.
David W. Thomas, et al., "Clinical Development Success Rates 2006-2015", BIO Industry Analysis, Jun. 2016, pp. 1-28.
"Early 2016 Outlook Report" BioMedTracker/MedDeviceTracker, 2016, pp. 1-29.
Stuart Wagner, "Pharma Q2 2016 Outlook Report (Biomedtracker)", LinkedIn, Apr. 22, 2016, p. 1.
Myoung Cha, et al., "Pharmaceutical forecasting: throwing darts?", Nature Reviews: Drug Discovery, vol. 12, Oct. 2013, pp. 737-738.
Percy H. Carter, et al., "Investigating investment in biopharmaceutical R&D", Nature Reviews: Drug Discovery, Advanced Online Publication, 2016, pp. 1-2.
International Search Report and Written Opinion of the International Searching Authority dated Oct. 22, 2018 in PCT/US18/00258 filed Aug. 17, 2018, 14 pages.
International Search Report and Written Opinion of the International Searching Authority dated Oct. 25, 2019, in PCT/US19/44681, 12 pages.

* cited by examiner

| drug_ii_s | disease_id | country | company_id | in_status | display_name | Special Designation | org_size | disease category | discount_reason_similar | "weighted" score | Predicted Probability |
|---|---|---|---|---|---|---|---|---|---|---|---|
| 67037 | 3399 | US | 29927 | PR | patisiran | | 1 Mld | Neurology/Psychiatric | N/A | 1.777719371 | 86% |
| 67037 | 3399 | EU | 29927 | PR | patisiran | | 1 Mld | Neurology/Psychiatric | N/A | 1.890477805 | 87% |

FIG. 10

APPARATUS, METHOD, AND COMPUTER-READABLE MEDIUM FOR DETERMINING A DRUG FOR MANUFACTURE

CROSS-REFERENCE TO RELATED APPLICATIONS

The present application claims priority to U.S. Provisional Application No. 62/714,446, filed Aug. 3, 2018, the teaching of which is hereby incorporated by reference in its entirety for all purposes.

BACKGROUND

Field of the Disclosure

The present disclosure relates to determination of a drug for manufacture.

Description of the Related Art

For patients in need, pharmaceutical manufacturers can provide lifesaving drugs or therapies. Delivering these drugs to patients, however, requires determining what drugs may enter the regulatory pathway and successfully exit as an approved drug ready for patients, a determination that can impact the next decade of research and development.

When done well, this determination can result in lifesaving drugs efficiently moving from the bench to the bedside and patients receiving the therapies they need. However, available clinical data, used as benchmarks, can be interpreted incorrectly or can otherwise mislead such decisions. An efficient approach in determination of drugs for manufacture is required.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to an apparatus, method, and computer-readable medium for determining a drug for manufacture.

According to an embodiment, the present disclosure further relates to an apparatus for determining a drug for manufacture, the apparatus being communicably coupled via a network to a manufacturing device, the apparatus comprising processing circuitry configured to receive input data related to one or more drug programs, the input data related to the one or more drug programs describing a drug, a disease indication, and a geo location associated with a development of the drug, acquire data from a database, based upon the input data, wherein the acquired data comprises chronological data and qualitative data of one or more historical drug programs, the qualitative data being related to characteristics of a clinical trial, generate one or more models based upon the acquired data from the database, wherein each of the one or more models is related to a chronological event, the chronological event being one or more dates related to the clinical trial, determine, from the one or more models, one or more outputs related to the chronological event, select, based upon the determined one or more outputs, one of the one or more drug programs for manufacture, and transmit, to the manufacturing device via the network, manufacturing information related to the manufacture of the drug of the selected one of the one or more drug programs.

According to an embodiment, the present disclosure further relates to a method for determining a drug for manufacture, comprising receiving, by processing circuitry, input data related to one or more drug programs, the input data related to the one or more drug programs describing a drug, a disease indication, and a geo location associated with a development of the drug, acquiring, by the processing circuitry, data from a database, based upon the input data, wherein the acquired data comprises chronological data and qualitative data of one or more historical drug programs, the qualitative data being related to characteristics of a clinical trial, generating, by the processing circuitry, one or more models based upon the acquired data from the database, wherein each of the one or more models is related to a chronological event, the chronological event being one or more dates related to the clinical trial, determining, by the processing circuitry, from the one or more models, one or more outputs related to the chronological event, selecting, by the processing circuitry, based upon the determined one or more outputs, one of the one or more drug programs for manufacture, and transmitting, by the processing circuitry, to a manufacturing device via a network, manufacturing information related to the manufacture of the drug of the selected one of the one or more drug programs.

According to an embodiment, the present disclosure further relates to a non-transitory computer-readable storage medium storing computer-readable instructions that, when executed by a computer, cause the computer to perform a method of determining a drug for manufacture, comprising receiving input data related to one or more drug programs, the input data related to the one or more drug programs describing a drug, a disease indication, and a geo location associated with a development of the drug, acquiring data from a database, based upon the input data, wherein the acquired data comprises chronological data and qualitative data of one or more historical drug programs, the qualitative data being related to characteristics of a clinical trial, generating one or more models based upon the acquired data from the database, wherein each of the one or more models is related to a chronological event, the chronological event being one or more dates related to the clinical trial, determining, from the one or more models, one or more outputs related to the chronological event, selecting, based upon the determined one or more outputs, one of the one or more drug programs for manufacture, and transmitting, to a manufacturing device via a network, manufacturing information related to the manufacture of the drug of the selected one of the one or more drug programs.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 10 is a probability of success of a drug in different regions, according to an exemplary embodiment of the present disclosure.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

When considering that one in ten drugs successfully traverse the regulatory pathway from Phase 1 to approval and, finally, to patients in need, the probability of success of a clinical trial can be important for clinical researchers and decision-makers to consider in determining an expedient way to bring an efficacious drug to a target patient population. Without up-to-date estimates of probability of success, however, or the timeline to achieve that success, stakeholders may misjudge the likelihood that a specific drug can reach patients quickly and, therefore, delay or even deny access to treatment for potentially thousands of patients in need.

One of the biggest challenges in estimating the success rate and time to success of clinical trials is access to accurate information on trial characteristics and outcomes. Gathering such data is expensive, time-consuming, and susceptible to error. Moreover, with current approaches, trained analysts may require thousands of hours to incorporate a corpus of reference data in order to produce probability of success and time to success estimates, wherein these estimates may comprise little more than predictions based upon historical averages.

To this end, an automated approach to determining a drug for manufacture, based upon characteristic traits and outcomes of prior clinical trials, is required such that new therapies may be efficaciously delivered to patients in need.

Figure 1:
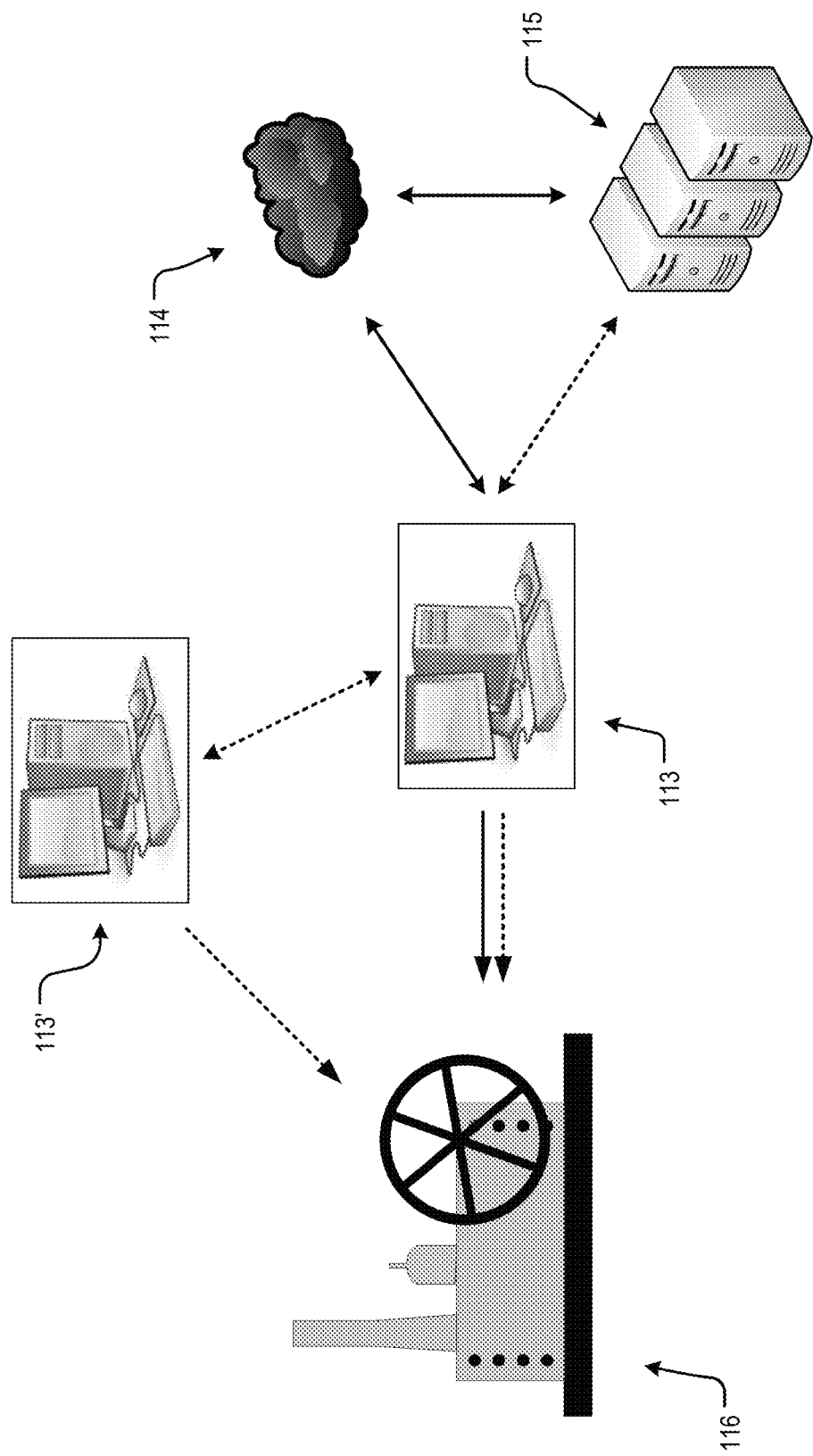
FIG. 1 is a schematic describing communication between components within a manufacturing process for a drug, according to an exemplary embodiment of the present disclosure.

According to an embodiment, generally, the present disclosure describes a method, or process, for determining a drug for manufacture. The terms "method" and "process" may be used interchangeably herein. Specifically, the present disclosure relates to determination of a drug for manufacture via predictive models that consider a variety of quantitative and qualitative traits to estimate chances of success and development timelines, wherein the determination of the drug for manufacture is based upon these estimations. With reference to FIG. 1, the development of predictive models for estimation of a probability of success and development timelines can be performed by a processing circuitry embodied within a computer, or, in an embodiment, a drug determining device 113. In an example, the drug determining device 113 can be a computer, a laptop, a tablet, or similar device configured to execute a method described herein and to be communicably-linked with one or more local servers 115 and one or more remote servers 114. The one or more local servers 115 and the one or more remote servers 114 can store or be configured to process quantitative information related to regulatory data including chronological data comprising dates of clinical trial milestones, clinical trial outcomes determined therefrom, and the like. Moreover, the one or more local servers 115 and the one or more remote servers 114, or the cloud, can further store or be configured to process qualitative information related to regulatory data and clinical trials including clinical trial sponsor strength, clinical trial sponsor type, clinical trial therapeutic area, and the like. It can be appreciated that regulatory data is non-limiting and can encompass chronological data including dates of clinical trial milestones, clinical trial outcomes determined therefrom, and the like, as well as developmental, or qualitative, data related to clinical trials including clinical trial sponsor strength, clinical trial sponsor type, clinical trial therapeutic area, and the like. In an embodiment, the drug determining device 113 may be one of a plurality of drug determining devices 113' communicably-linked, locally or remotely, such that development of predictive models may be expedited via parallel processing or, for example, instructions derived therefrom may be communicated.

According to an embodiment, the drug determining device 113 can be a computer having a display and a user interface such that the development of a predictive model can be initiated. Initiation can include providing, to the drug determining device 113, information relating to a drug, a therapeutic indication, a country, and/or a company of interest. In an example, and in order to determine the most efficacious pathway to reach a patient population with a particular indication, a user may provide a plurality of data inputs to the drug determining device 113 wherein the therapeutic indication, the country, and the company are constant while the plurality of changing data inputs includes a plurality of different drugs. In this instance, the drug determining device 113 may develop a plurality of predictive models to estimate chances of success and development timeline for each of the plurality of different drugs in the context of the constant data inputs. From these developed models, the drug determining device 113 may determine, based upon the probability of success and the development timeline from each of the developed models, one drug of the plurality of different drugs to be most likely to successfully reach patients. With this determination, the drug determining device 113 may transmit information related to the determined drug to a manufacturing device 116 to begin producing the determined drug in preparation for clinical trials. In an embodiment, the transmission of the determined drug to the manufacturing device 116 begins production. In an embodiment, the manufacturing device 116 is a device controlled by a third party and actions beyond transmission of the determined drug to the manufacturing device 116 are handled accordingly.

Figure 2:
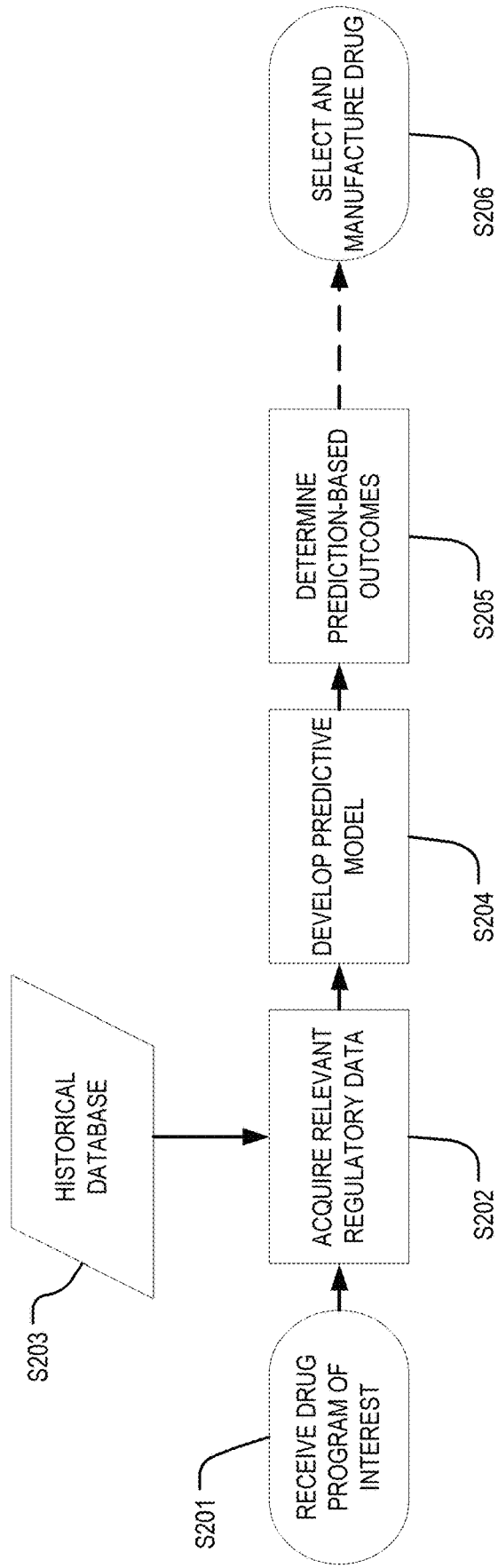
FIG. 2 is a high-level flowchart describing a manufacturing process for a drug, according to an exemplary embodiment of the present disclosure.

The method implemented by the drug determining device 113 to determine the drug to be manufactured, in the context of FIG. 1, requires, for each drug program of a plurality of drug programs, the identification of a drug program, the acquisition of relevant regulatory data, and the development of a plurality of models estimating probabilities of success and predicted timelines at developmental milestones. FIG. 2 is high-level flowchart of the above described process as applied to a single drug program. With reference to FIG. 2, initially, a user-defined information related to a drug program of interest can be received S201. In an example, the user-defined information related to a drug program of interest can be related to a preclinical drug of interest or a clinical drug currently in clinical trials. The user-defined drug program of interest can be indicated via the user interface of the drug determining device. In an embodiment, the drug program of interest can be described by information related to a drug, an indication, a country, a company, and the like. In an embodiment, the drug program of interest can be described by information related to an indication only. In an embodiment, the drug program of interest can be further described by a specific developmental milestone including, among others, Phase 0 to approval, Phase 1 to Phase 2 transition, or filing to approval.

According to an embodiment, having received the user-defined drug program of interest, the drug determining device can acquire relevant regulatory data S202. The relevant regulatory data can be a subset of a historical database S203 comprising a corpus of information related to the development of one or more drug programs. In an embodiment, the acquired relevant regulatory data can describe drug programs representative of the user-defined drug program of interest. In an example, the acquired relevant regulatory data can be chronological data of drug development, wherein success or failure in a phase transition, for example, can be determined by the presence or absence of phase start dates. In an example, the acquired relevant regulatory data can be qualitative data of drug development, the qualitative data of drug development being factors that may impact the chronological data of drug development. From the acquired relevant regulatory data from the historical database, one or more predictive models can be developed S204 according to the user-defined drug program of interest. In an example, a user-defined drug program of interest includes development of a drug from Phase 1 to approval, wherein a predictive model can be required for each milestone therein, including Phase 1 (P1) to Phase 2 (P2), P2 to Phase 3 (P3), P3 to filing, filing to approval, and the like. In an example, a user-defined drug program of interest can include development of a drug from preclinical studies to approval, wherein a predictive model can be required for each milestone therein, including preclinical (P0) to P1, P1 to P2, P2 to P3, P3 to filing, and filing to approval. From each predictive model, the drug determining device can determine prediction-based outcomes S205 for each milestone such that a probability of success and timeline can be estimated. These determined prediction-based outcomes can be considered in context of each of a plurality of drug programs of interest identified by a user such that one of the plurality of drug programs may be selected for manufacture S206. The high-level description provided above of the method implemented by the drug determining device is further detailed below.

Figure 3:
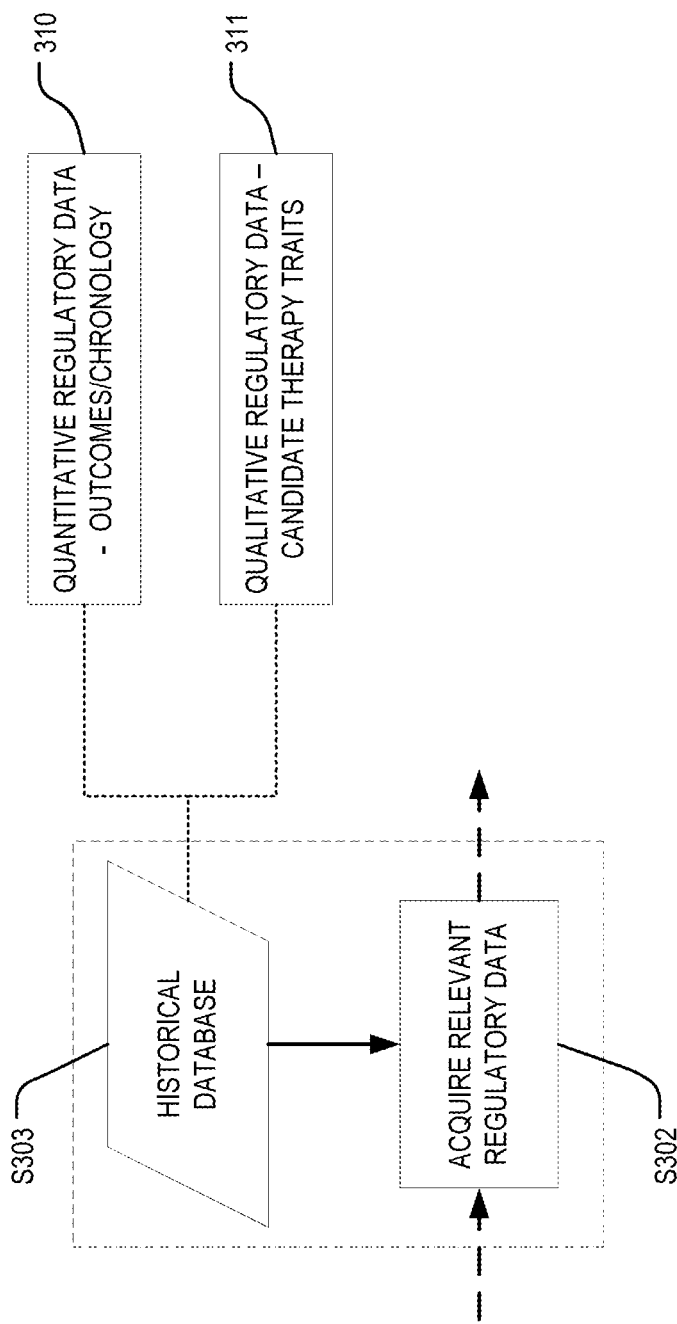
FIG. 3 is a low-level schematic of an aspect of a manufacturing process for a drug, according to an exemplary embodiment of the present disclosure.

FIG. 3 is a low-level description of an aspect of a method of the drug determining device. Following receipt of the user-defined drug program of interest, or, for example, the user-defined drug program of interest of the plurality of drug programs of interest, the drug determining device can acquire relevant regulatory data S302. In an embodiment, the relevant regulatory data S302 may come from a historical database S303, the historical database including a corpus of data related to drug development. In an embodiment, the historical database may comprise data acquired from public or private databases such that predictive-models are longitudinally dynamic. The corpus of data related to drug development within the historical database can include quantitative regulatory data 310, qualitative regulatory data 311, and the like. In an embodiment, the quantitative regulatory data 310 and the qualitative regulatory data 311 can be related such that corresponding quantitative values and qualitative traits are related and can be accessed as such.

According to an embodiment, quantitative regulatory data 310 may comprise information related to the success or failure of a specific milestone of drug development. In an example, the quantitative regulatory data 310 can include successful completion of P1 of drug development but failure of P2 of drug development. Moreover, the quantitative regulatory data 310 may comprise information related to the timeline of drug development. In an example, the quantitative regulatory data 310 can include the date at which an application for approval of a new drug is filed, referred to as a New Drug Application (NDA) in the United States and Japan and a Marketing Authorization Application in Europe, and the date at which the application has been approved. Qualitative regulatory data 311 can include traits describing the drug program including, among others, the use of biomarkers to define a patient population. Table 1 provides an exemplary list of qualitative regulatory data 311 that can be considered during model development and evaluation of predictive value of said models.

TABLE 1

Exemplary List of Qualitative Regulatory Data

| Qualitative Regulatory Data - Traits | Considered Aspect |
|---|---|
| Alliance status | Being developed by originator; under a partnership or in-license |
| Is drug already successful for other disease/country/company? | Repositioned? |
| Is drug reformulation or combination of approved drugs? | Reformulated, combination, or novel formulation? |
| Level of target validation | Disease target evidentially linked to disease outcome? |
| Reasons similar development programs have been discontinued | Safety; efficacy; etc. |
| Sponsor size | Large, medium, small |
| Special regulatory designation | Fast Track, Breakthrough Therapy, etc. |
| Therapeutic area | Cancer; infectious disease; inflammatory disease; etc. |
| Type of drug compound | Biological therapeutic; small molecule therapeutic |
| Sponsor strength | Count of drug programs |
| Sponsor type | Public; private |
| Clinical trials estimated end dates | Estimated trial duration |
| Clinical trials estimated primary endpoint completion dates | Estimated trial primary endpoint duration |
| Clinical trials average patient count | Average patient counts |
| Use of biomarkers to define patient population | Biomarker_type = 'Disease marker' |

During model development, as will be discussed later, qualitative regulatory data 311 can be included or excluded in any given model based upon the significance each trait has on model accuracy. Further, it can be appreciated that the qualitative regulatory data 311 described in Table 1 is non-limiting and merely representative of a variety of traits relevant to drug development. In an embodiment, additional qualitative regulatory data 311 can include regulatory committee meetings, company reports, drug target families, and the like. Moreover, qualitative regulatory data 311 providing further description of drug compounds, including mechanism of action, drug size, hydrophobicity, functional groups, and the like, can be considered.

According to an embodiment, one or more of the qualitative regulatory traits 311 may be parasitic, synergistic, and the like, such that the presence of one may have a multiplicative impact on another, or similar effect, as would be understood by one of ordinary skill in the art. In an example, there may be a positive interaction between a "large" sponsor size and a "biological therapeutic" type of drug compound, wherein a large sponsor may have sufficient resources to fully develop a larger, biological therapeutic that may have less predictable clinical outcomes. Moreover, in certain cases, the presence of one trait may exclude the relevance of another trait. For example, a special regulatory designation such as "a breakthrough therapy" may make irrelevant traits such as "reasons similar development programs have been discontinued". In an example, there may be a negative interaction between a "public" sponsor type and clinical trials estimated primary endpoint completion dates, understanding that a "public" sponsor may be more risk averse and thus, more cautious in planning and execution of clinical trials.

Figure 4:
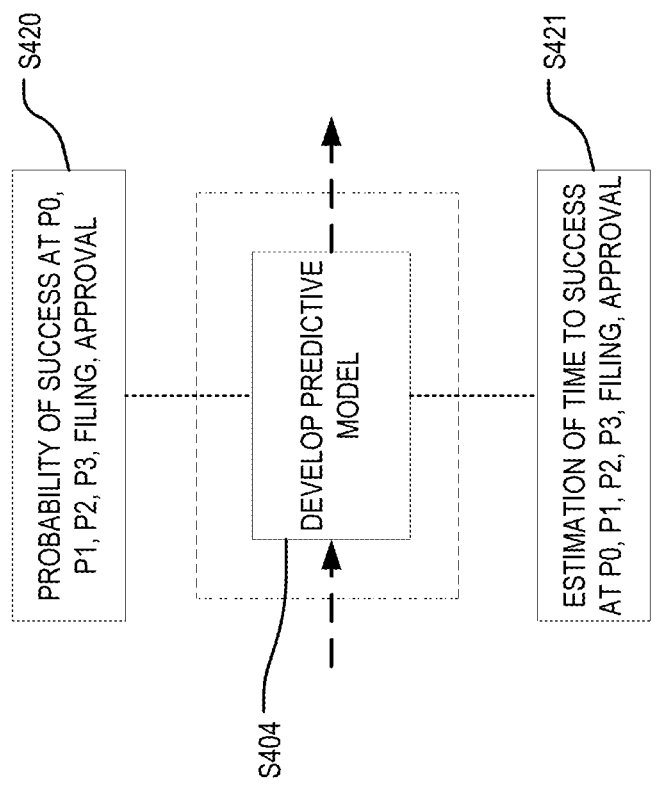
FIG. 4 is a low-level schematic of an aspect of a manufacturing process for a drug, according to an exemplary embodiment of the present disclosure.

Having acquired relevant regulatory data, with reference to FIG. 4, predictive models may be developed S404, as appropriate, via the drug determining device. In the example wherein a drug program is evaluated from P0 to approval, a plurality of predictive models can be developed to describe each milestone within drug development. For instance, in order to estimate a probability of success, from P0 to approval, of a given drug program, predictive success models S420 can be developed describing the probability of successful transition from P0 to P1, from P1 to P2, from P2 to P3, from P3 to filing, from filing to approval, and the like. For each success model, qualitative regulatory data can be considered individually and in combination, in context of quantitative regulatory data including, for example, outcomes, to develop a success model that is most accurately predictive of outcomes. Similarly, in order to estimate a time to success, from P0 to approval, of a given drug program, predictive timeline models S421 can be developed describing the timeline of dates related to successful P0, P1, P2, P3, filing, approval, and the like. For each timeline model, qualitative regulatory data can be considered individually and in combination, in context of quantitative regulatory data including, for example, outcome timelines, to develop a timeline model that is most accurately predictive of drug program chronology.

As suggested, according to an embodiment, the drug determining device can be configured to develop one or more predictive models. In an example, the one or more predictive models can be eight predictive models describing P1 success probability, P2 success probability, P3 success probability, filing success probability, P1 timeline, P2 timeline, P3 timeline, approval timeline, and the like. Similarly, in an example, the one or more predictive models can be ten predictive models describing P0 success probability, P1 success probability, P2 success probability, P3 success probability, filing success probability, P0 timeline, P1 timeline, P2 timeline, P3 timeline, approval timeline, and the like.

Figure 5A:
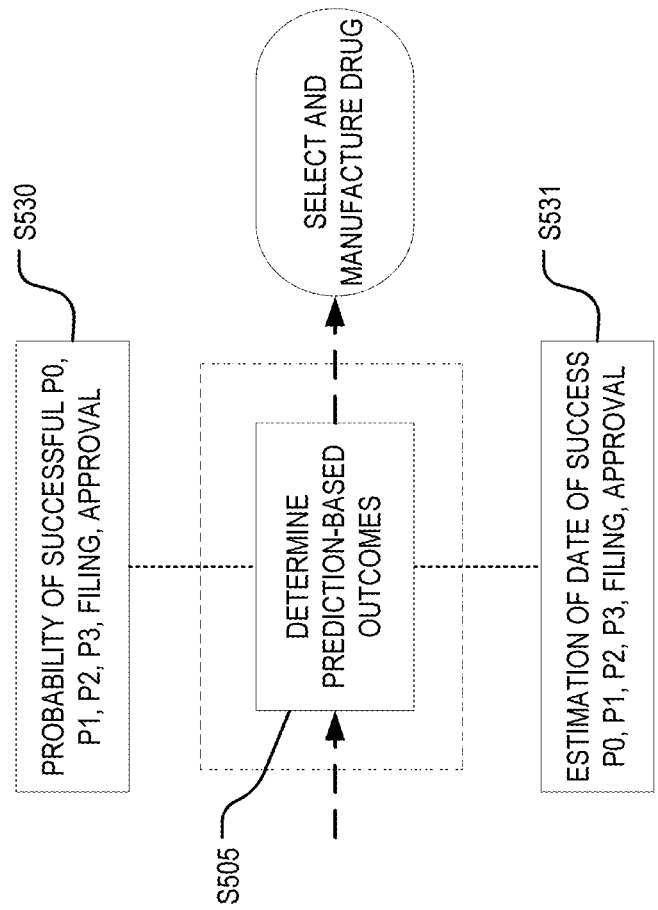
FIG. 5A is a low-level schematic of an aspect of a manufacturing process for a drug, according to an exemplary embodiment of the present disclosure.

Each of the plurality of the developed predictive models can be evaluated, via the drug determining device, to determine prediction-based outcomes, as described in FIG. 5A. In an embodiment, determination of prediction-based outcomes S505 can include determining the probability of success of a drug moving from P0 through P1, P2, P3, and filing to approval S530 from the developed predictive-models. In an embodiment, determination of prediction-based outcomes S505 can include determining an estimation of time to success of a drug moving from P0 through P1, P2, P3, and filing to approval S531.

Figure 5B:
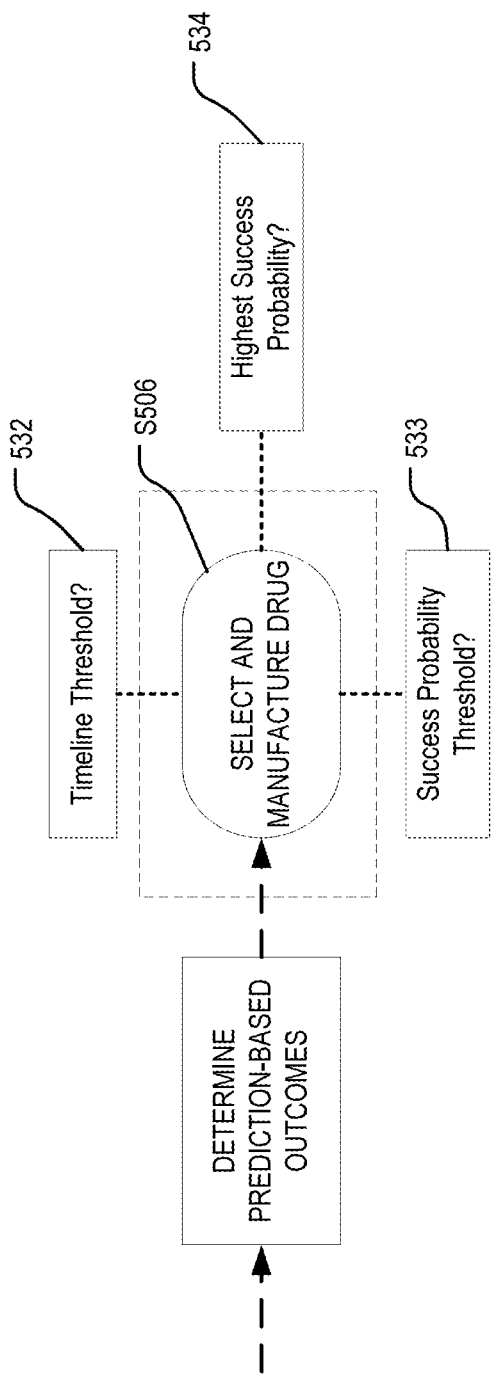
FIG. 5B is a low-level schematic of an aspect of a manufacturing process for a drug, according to an exemplary embodiment of the present disclosure.

According to an embodiment, the determined prediction-based outcomes for each of the plurality of developed predictive models can be analyzed such that a drug for manufacture can be determined. With reference to FIG. 5B, the prediction-based outcome can be an outcome describing the probability of success and the time to success from pre-clinical research to approval of an application for a new drug. In this context, and in order to determine the drug for manufacture if only a single drug program of interest has been identified, the drug program of interest can be selected S506 according to a comparison with one or more metrics. In an embodiment, the drug program for manufacture can be selected based upon a comparison with a timeline threshold 532, wherein the timeline threshold 532 is a maximum estimated time for a drug to move from pre-clinical research to approval. In an example, wherein the timeline threshold 532 is 14 years and a drug program of interest is estimated to reach approval in 12.5 years, the drug determining device can determine that the drug program of interest should proceed to manufacture.

In an embodiment, the drug program for manufacture can be selected based upon a comparison with a success probability threshold 533, wherein the success probability threshold 533 is a minimum probability of success of a drug program moving from pre-clinical research to approval. In an example, where the success probability threshold 533 is 90% and a drug program of interest is estimated to have a 92% probability of success, the drug determining device can determine that the drug program of interest should proceed to manufacture.

Moreover, the above-described prediction-based outcome can be one of a plurality of prediction-based outcomes describing the probability of success and the time to success of one or more drug programs. In this context, and in order to determine a drug for manufacture, one of the one or more of drug programs can be selected S506 according to one or more metrics. In an embodiment, the one or more metrics can be, among others, a highest probability of success 534. In an example, wherein prediction-based outcomes of four drug programs of interest, from P0 to approval, are determined, the drug program of the one or more drug programs with the highest estimated probability of success can be selected for manufacture S506.

According to an embodiment, the above-described thresholds and related criteria for drug program selection can be determined such that drug development and, as a result, safe delivery of lifesaving drugs, can be expedited. In an embodiment, the above-described thresholds and related criteria for drug program selection can be determined by the drug determining device based on a particular company's previously-used thresholds, particular company's geographical location, other comparable (or similar) companies' geographical locations/thresholds of corresponding qualitative traits, or the like. This approach allows for more robust threshold selection thereby providing improved (and more realistic) results, while minimizing time and eliminating possible unrealistic thresholds that may otherwise be input.

In an example, a user is interested in addressing an indication, wherein the user would like to bring a drug from P1 through approval. In an example, the indication is osteoarthritis, and the user defines an interest in developing a therapy for osteoarthritis in the United States. This information can be provided to a drug determining device such that a remaining two user-defined inputs, drug and company, remain dynamic. Next, the drug determining device acquires relevant regulatory data from a historical database. In an example, this can include information related to drug programs directed to osteoarthritis developed in the United States, wherein the drug being developed and the company developing the drug are dynamic parameters that may change for each drug program. Having identified a plurality of drug programs directed towards osteoarthritis within the United States, matched qualitative data and quantitative data for each drug program is organized such that quantitative features including drug program success, time to success and the like are program-matched with qualitative features including regulatory designation, sponsor type, and the like. In an example, regulatory data from one hundred drug programs can be acquired from the historical database directed to osteoarthritis drug development in the United States. In arranging the data from the one hundred drug programs, the acquired data can be separated by each of four drugs used, wherein, for example, each drug was used in one of twenty five drug programs. In total, each of the one hundred drug programs, naturally, achieves varying milestones along the development timeline, with some reaching, for example, approval and others being discontinued after P1.

In order to determine the likelihood that a specific drug of the four drugs will reach approval, a predictive model can be developed for each of the four drugs, wherein regulatory traits determined to be the best predictors, individually and in combination, are selected for model development. In an example, as related to the biological therapeutic interleukin-receptor antagonist (IL-1ra), a generated model can be evaluated to determine that IL-1ra has a 57% probability of reaching approval from P1. As related to a small molecule therapy dexamethasone, a generated model can be evaluated to determine that dexamethasone has an 87% probability of reach approval from P1. Similar models can be developed and evaluated for the remaining drugs identified from the acquired regulatory data.

Having determined a probability of success for each of the four drugs identified, the drug determining device can select, based upon the determined probability of successes, that dexamethasone has the highest likelihood of reaching approval from Phase 1 as a therapy for osteoarthritis in the United States. Therefore, in order to reach patients in need expediently, this selection can be transmitted, via a communication network, to a manufacturing or fabrication device for production in preparation for a clinical trial.

According to an embodiment, a user may be a client with one or more drug programs currently in clinical trials. In an example, the client may be a drug manufacturer with four active drug programs, each drug program being in a different phase of the regulatory process (e.g. P1, P2, P3, etc.). Further, the user may be interested in determining which of the four active drug programs should be given primary focus and pushed toward approval. This determination can be made based upon development of a success model and a timeline model for each drug program, from their current phase of development to approval, and a subsequent comparison of the outputs in order to determine which drug program to move forward. To this end, and it relates to the field of oncology, the user may indicate drug development programs including four clinical trials implementing a vascular endothelial growth factor A (VEGF-A) antibody, each of the four drug programs being directed to a separate indication of solid tumors including non-small cell lung cancer, colorectal cancer, hepatocellular carcinoma, and osteosarcoma. Accordingly, this information, including the country of development, can be provided to a drug determining device such that relevant regulatory data can be acquired from a historical database. In an example, this can include information related to VEGF-A antibodies and can include information related to the above-listed solid tumor cancers. Having identified a plurality of drug programs related to the above parameters, quantitative data and qualitative data for each drug program is organized such that quantitative features including drug program success, time to success, and the like, are program-matched with qualitative features including regulatory designation, sponsor type, and the like. In an example, regulatory data from one hundred drug programs can be acquired from the historical database directed to drug development of the above-described therapy and the above-described indications in, for example, the United States. In arranging the data from the one hundred drug programs, the acquired data can be separated into twenty five drug programs directed to each of the four indications targeted, wherein a VEGF-A antibody was used in each of twenty five drug programs. In total, each of the one hundred drug programs, naturally, achieves varying milestones along the development timeline, with some reaching, for example, approval and others being discontinued after P1.

In order to determine the likelihood that one of the disease indications may proceed to approval, a predictive model can be developed for each of the four indications, wherein regulatory traits determined to be the best predictors, individually and in combination, are selected for model development. In an example, as related to colorectal cancer, a generated model can be evaluated to determine that a VEGF-A antibody has a 57% probability of reaching approval from P1. As related to an osteosarcoma, a generated model can be evaluated to determine that a VEGF-A antibody has a 64% probability of reaching approval from P2. Similar models can be developed and evaluated for the remaining two indications identified in the acquired regulatory data. Moreover, the drug determining device can develop models estimating time to success of each indication. In an example, time to success models estimate that a VEG-F antibody applied to osteosarcoma will reach approval more quickly.

Having determined a probability of success and a time to success for VEGF-A in each of the four indications identified, the drug determining device can select, based upon the determined outputs, that osteosarcoma has the highest likelihood of most expediently reaching approval from Phase 2 as a therapy in the United States. Therefore, in order to reach patients in need as quickly as possible, this selection can be transmitted to a manufacturing or fabrication device for production of the drug in appropriate quantities in preparation for a next phase of a clinical trial.

Figure 6A:
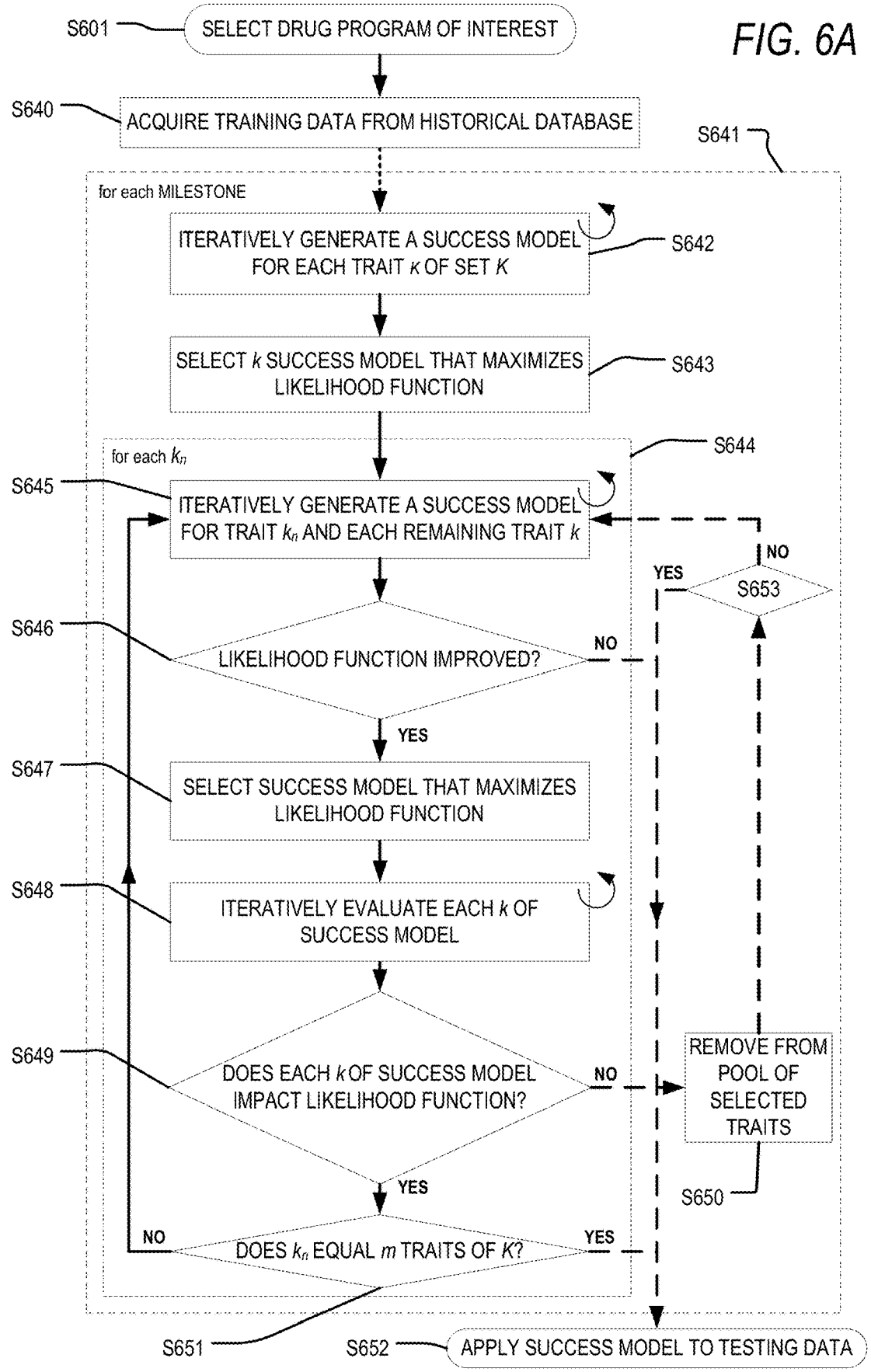
FIG. 6A is a high-level flowchart describing development of a success model of a drug, according to an exemplary embodiment of the present disclosure.

The above-described process implemented by the drug determining device includes the development of a plurality of predictive models pertaining to a drug development milestone of interest and related to one or more drug programs of interest. With reference to FIG. 6A, according to an embodiment of the present disclosure, a flowchart for developing a success model of a drug program is described, wherein the development of the success model, performed by the drug determining device comprises a training phase and a testing phase. First, one of one or more drug programs of interest can be identified or received from the user, by the drug determining device, via the user interface S601. Next, relevant regulatory data can be acquired from a historical database S640 comprising a corpus of reference regulatory data, as described herein. In an embodiment, the relevant regulatory data includes drug program data corresponding to matched quantitative data and qualitative traits. During development, the relevant regulatory data can be divided into training data and testing data in a way that appropriately trains a success model to predict outcomes as reported in the testing data.

According to an embodiment, in selecting a drug program of interest, it can be indicated, via user interface (the input being received by the drug determining device), that outcome prediction for success probability and time to success for each milestone with a drug development timeline is desired. Therefore, as related to a success model, the success model development process described below describes an iteration of success model development at a specific milestone. It can be appreciated that a similar process can be followed to develop a success model for each of the remaining milestones identified during the drug program selection process S641. Moreover, it can be appreciated that, in the instance that one or more drug programs have been identified, a similar process can be followed to develop a success model for each of the remaining drug programs identified during the drug program selection process such that a determination of a drug for manufacture can be made.

Generally, with respect to the training phase, and according to an embodiment, in developing a success model, qualitative regulatory traits, in context of corresponding quantitative regulatory data, can be considered. According to an embodiment, and as would be understood by one of ordinary skill in the art, a logistic regression model can used to estimate the success probability of each phase transition. When all traits, including composite traits that may be parasitic, synergistic, or otherwise combinatory of other traits, are considered, the probability of success for each drug program, can be estimated by $$p = \frac{1}{(1 + e(-(w_1 k_1 + w_2 k_2 + w_3 k_3 + \ldots + w_m k_m)))} \quad (1)$$

wherein p is the probability of success considering m traits, w is a coefficient associated with a corresponding trait k, and m is the total number of traits.

Specifically, with reference again to FIG. 6A, for each drug development milestone of interest S641, a step-wise method for determining n statistically significant traits, wherein n is less than or equal to the total number of traits m, can be performed. First, for each trait k in all considered traits of set K, a predictive model of success can be generated for $k_1, k_2, k_3 \ldots, k_m$ S642. Among the generated m models from S642, the trait k that most significantly improves a likelihood function can be selected into a pool of selected traits S643. Having selected the trait $k_1$, the number of selected traits, or n, is equal to one, and the number of remaining traits of the total number of traits of set K, is equal to m−n, or m−1. For each of the remaining m−n traits in set K, a subsequent predictive model of success can be generated for $k_1$ and $k_2, k_3, \ldots, k_{m-n}$ S645. In an embodiment, for each of the remaining m−n traits in set K, a subsequent predictive model of success can be generated for $k_n$ and $k_{n+1}, k_{n+2}, \ldots k_{m-n}$. Each of the m−n generated models can be evaluated to determine if any model is statistically significant in the context of improving a likelihood function S646. If the drug determining device determines that no subsequent predictive model of success can be generated such that the likelihood function is improved, success model development is stopped and the current success model can be applied to testing data S652. If, however, the drug determining device determines that one or more traits does improve the likelihood function, the trait that most improves the likelihood function can be selected for the pool of selected traits S647. At S647, the number n of selected traits increases by one. To determine if each one of the select traits is necessary for the success model, each of the traits in the pool of selected traits can be evaluated for significance S648. Specifically, the impact of each trait of the pool of selected traits on the likelihood function can be determined S649. If the drug determining device determines that all traits impact the likelihood function, success model development continues to S651, wherein, if the number of selected traits n is less than the total number m of traits within the set K, development returns to S645. Conversely, if the number of selected traits n is equal to the total number m of traits within the set K, development ends and the current success model can be applied to testing data S652. If, however, at S649, the drug determining device determines that one or more traits of the pool of selected traits no longer impacts the likelihood function, each of the one or more traits can be removed from the pool of selected traits S650. Moreover, upon removing each of the one or more traits from the pool of selected traits, the remaining, current pool of selected traits can be compared with each of the previous pools of selected traits S653. If, upon comparison at S653, the drug determining device determines that the current pool of selected traits is equal to a previous pool of selected traits, success model development can be stopped and the current success model can be applied to testing data S652. Alternatively, if the current pool of selected traits is different from any of the previous pools of selected traits, success model development returns to S645.

Figure 6B:
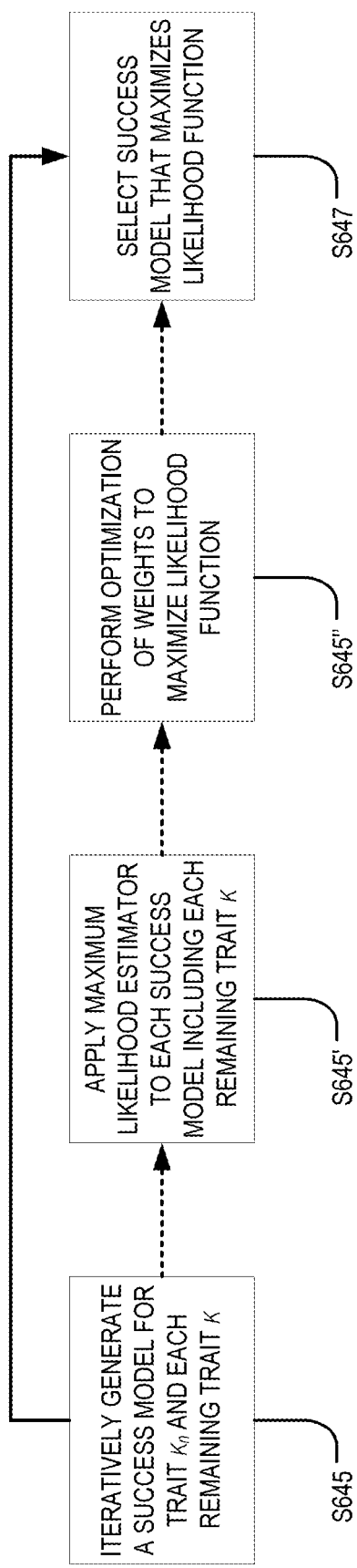
FIG. 6B is a low-level flowchart of an aspect of development of a success model of a drug, according to an exemplary embodiment of the present disclosure.

According to an embodiment, a maximum likelihood estimation can be used to determine an optimal set of coefficients ($w_1, w_2, \ldots w_m$) of Eq. (1) and to evaluate the predictive benefit of including or excluding traits in the success model, as described in FIG. 6A. To this end, FIG. 6B is a low-level flowchart describing implementation of a maximum likelihood estimate in determining the success model described in FIG. 6A. According to an embodiment, FIG. 6B is described with respect to two or more selected traits, but it can be appreciated that a similar approach can be implemented with respect to a single selected trait, mutatis mutandis. Generally, following generation S645 of a success model for each trait $k_n$ and each remaining trait k of set K, and prior to selection of a maximal success model S647, a maximum likelihood estimator is applied to each generated success model to determine the predictive power of each success model. First, a maximum likelihood estimator can be applied to each success model S645'. Next, each weight w can be optimized in order to maximize each likelihood function S645". Having optimized each likelihood function, and considering each likelihood function associated with the success models, the success model that maximizes the likelihood function, and thus, the likelihood that an expected outcome happens, is selected for continued use within the development of the success model S647.

Specifically, according to an embodiment, a likelihood function can be determined for a training data set consisting of t drug programs. For the training data set consisting of t drug programs, a likelihood function corresponding to a real success or a real failure can be defined. For example, for each drug program i, where i=1, 2, 3, . . . , t, the likelihood of a success can be defined as $L_i = p_i$, where L is the likelihood of the outcome and p is the probability of the outcome. Further, for each drug program i, where i=1, 2, 3, . . . , t, the likelihood of a failure can be defined as $L_i = 1 - p_i$. Each individually defined drug program i can be further expressed as a combined set, where $L = L_1 * L_2 * L_3 * \ldots * L_t$ for i=1, 2, 3, . . . , t. Having defined individual likelihood functions and a combined likelihood function, a numerical optimization method can be implemented to determine optimal weights including, among others, the Newton-Raphson method.

As applied in the present disclosure, the above-described approaches improve efficiency and overall speed in model development as implemented in the drug determining device. Accordingly, this improves the functioning of the device (or computer), itself. In addition to the logistic regression model employed herein to estimate success probability, it can be appreciated that similar approaches within a class of classification models, can be implemented to the same effect, as would be understood by one of ordinary skill in the art.

Figure 7:
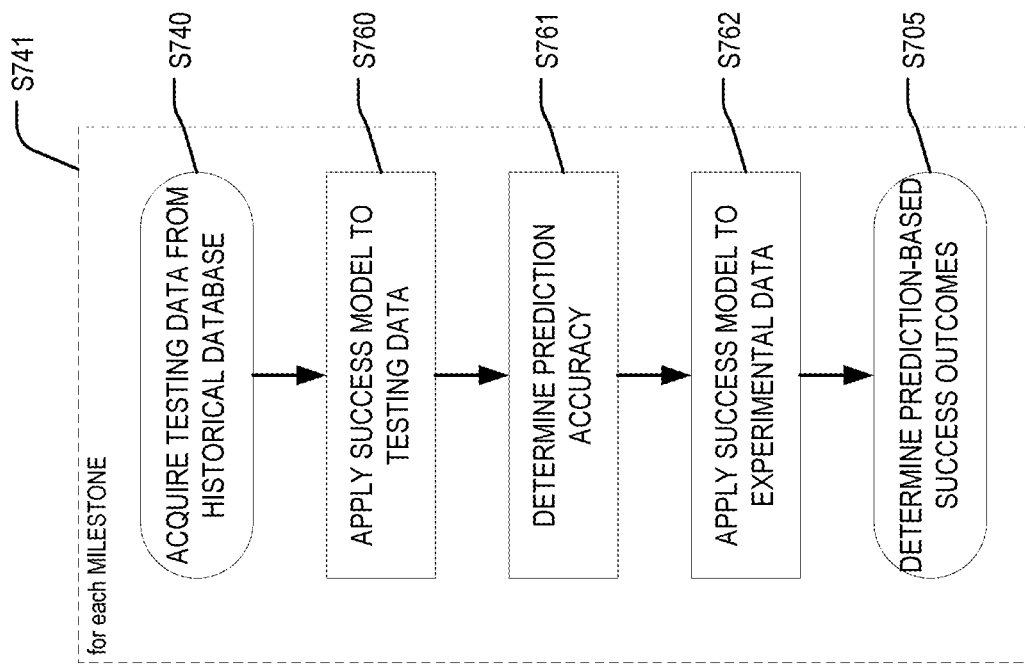
FIG. 7 is a high-level flowchart describing development of a success model of a drug, according to an exemplary embodiment of the present disclosure.

According to an embodiment, the training phase of success model development described in FIGS. 6A and 6B as related to, for example, P1 to P2, can next be evaluated by application to testing data, as described in FIG. 7. Again, the testing phase of success model development can be performed on each of a plurality of milestones S741 selected during drug program selection. As related to a single milestone, first, testing data previously acquired prior to the training phase can be recalled S740. Next, the success model developed during the training phase can be evaluated with the testing data S760. If the drug determining device determines that the success model does not provide an adequate level of prediction accuracy S761, additional regulatory data can be added to the training data such that the success model can be improved and the level of prediction accuracy can be increased. In an embodiment, the adequate level of prediction accuracy is a user-defined threshold based upon factors including, among others, therapeutic indication. If, however, the drug determining device determines that the success model provides an adequate level of prediction accuracy S761, the success model can provide an estimated probability of success S705 such that it can be utilized in determining the drug for manufacture. In an embodiment, the success model can be applied to additional experimental data, as requested by a user S762, in order to provide an estimated probability of success S705 such that it can be utilized in determining the drug for manufacture.

According to an embodiment, and substantially similar to the process described above for a success model, a timeline model can be developed to provide an estimation for time to success of a drug, and, therefore, can impact a determination of a drug for manufacture.

Figure 8A:
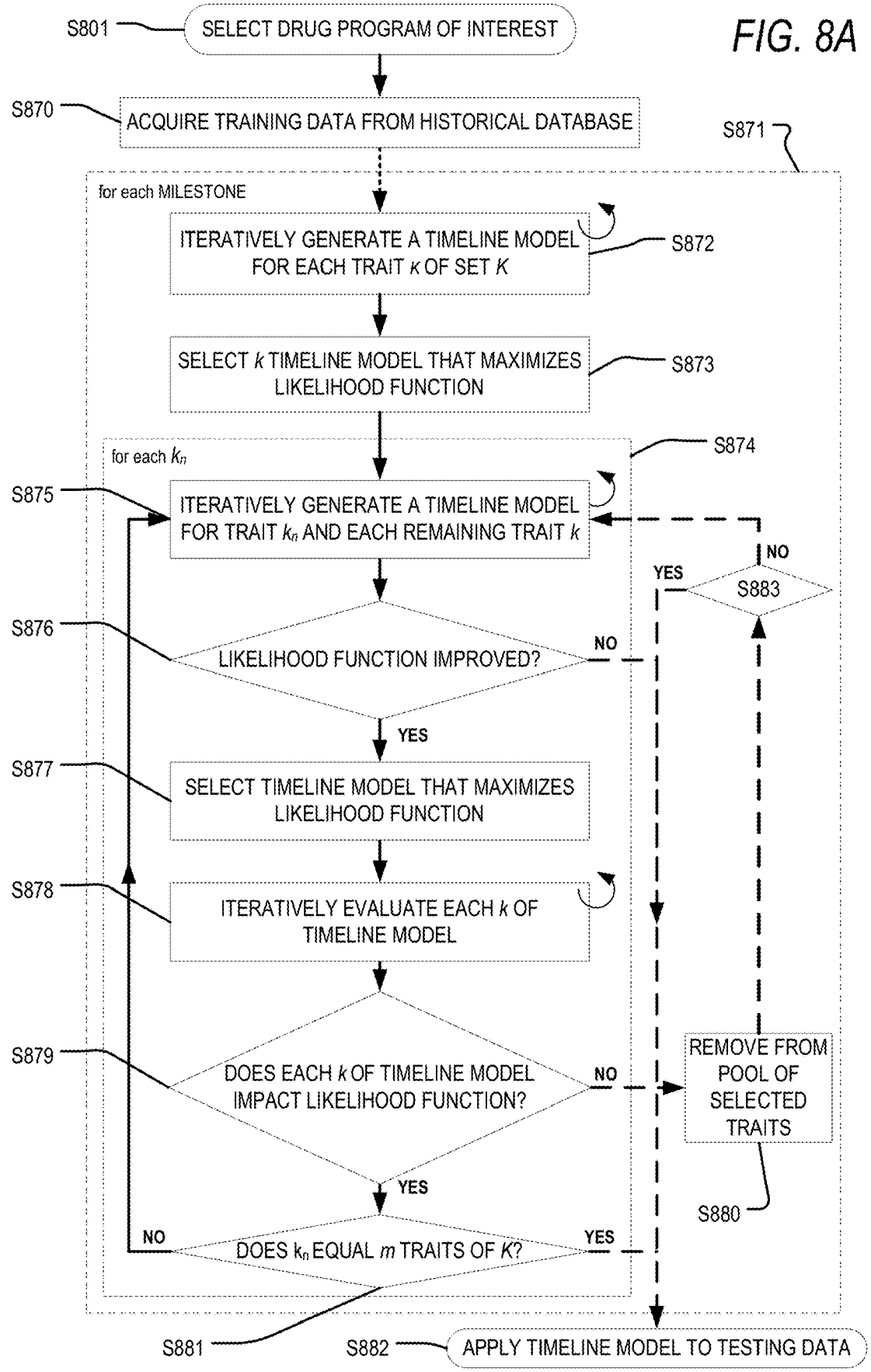
FIG. 8A is a high-level flowchart describing development of a timeline model of a drug, according to an exemplary embodiment of the present disclosure.

With reference to FIG. 8A, according to an embodiment of the present disclosure, a flowchart for developing a timeline model of a drug program is described, wherein the development of the timeline model comprises a training phase and a testing phase. First, one of one or more drug programs of interest can be identified or received from the user, by the drug determining device, via the user interface S801. Next, relevant regulatory data can be acquired from a historical database S870 comprising a corpus of reference regulatory data, as described herein. In an embodiment, the relevant regulatory data includes drug program data corresponding to matched quantitative data and qualitative traits. During development, the relevant regulatory data can be divided into training data and testing data in a way that appropriately trains a timeline model to predict time to success outcomes as reported in the testing data.

According to an embodiment, in selecting a drug program of interest, it can be indicated that outcome predictions for success probability and time to success for each milestone with a drug development timeline can be desired. Therefore, as related to a timeline model, the timeline model development process described below describes an iteration of timeline model development at a specific milestone. It can be appreciated that a similar process can be followed to develop a timeline model for each of the remaining milestones identified during the drug program selection process S871. Moreover, it can be appreciated that, in the instance that one or more drug programs have been identified, a similar process can be followed to develop a timeline model for each of the remaining drug programs identified during the drug program selection process such that a determination of a drug for manufacture can be made.

Generally, with respect to the training phase, and according to an embodiment, in developing a timeline model, qualitative regulatory traits, in context of corresponding quantitative regulatory data, can be considered. According to an embodiment, a survival model or, as described in the present disclosure, a proportional hazard model, can be used to estimate the timeline of each phase transition, as would be understood by one of ordinary skill in the art. When all traits, including composite traits that may be parasitic, synergistic, or otherwise combinatory of other traits, are considered, the rate of event occurrence, referred to as, for example, a hazard function, at a specific time t, can be expressed as $$H(t)=H_0(t)*e(w_1k_1+w_2k_2+w_3k_3+ \ldots +w_mk_m) \quad (2)$$

where $H(t)$ is a hazard function considering n traits, $H_0(t)$ is a baseline hazard value which is identical across all drug programs, w is a coefficient assigned to a corresponding trait k, and m is the total number of traits.

Specifically, with reference again to FIG. 8A, for each drug development milestone of interest S871, a step-wise method for determining n statistically significant traits, where n is less than or equal to m, can be performed. First, for each trait k in all considered traits of set K, a predictive timeline model can be generated for $k_1, k_2, k_3, \ldots, k_m$ S872. Among the generated m models from S872, the trait k that most significantly improves a likelihood function can be selected into a pool of selected traits S873. Having selected the trait $k_1$, the number of selected traits, or n, is equal to one, and the number of remaining traits of the total number of traits of set K, is equal to m-n, or m-1. For each of the remaining m-n traits in set K, a subsequent predictive timeline model can be generated for $k_1$ and $k_2, k_3, \ldots, k_{m-n}$ S875. In an embodiment, for each of the remaining m-n traits in set K, a subsequent predictive timeline model can be generated for $k_n$ and $k_{n+1}, k_{n+2}, \ldots, k_{m-n}$. Each of the m-n generated models can be evaluated to determine if any model is statistically significant in the context of improving a likelihood function S876. If the drug determining device determines that no subsequent predictive timeline model can be generated such that the likelihood function is improved, timeline model development can be stopped and the current timeline model can be applied to testing data S882. If, however, the drug determining device determines that one or more traits does improve the likelihood function, the trait that most improves the likelihood function can be selected for the pool of selected traits S877. At S877, the number n of selected traits increases by one. To determine if each one of the select traits is necessary for the timeline model, each of the traits in the pool of selected traits can be evaluated for significance S878. Specifically, the impact of each trait of the pool of selected traits on the likelihood function is determined S879. If the drug determining device determines that all traits impact the likelihood function, timeline model development continues to S881, wherein, if the number of selected traits n is less than the total number m of traits within the set K, development returns to S875. Conversely, if the number of selected traits n is equal to the total number m of traits within the set K, development ends and the current timeline model can be applied to testing data S882. If, however, at S879, the drug determining device determines that one or more traits of the pool of selected traits no longer impacts the likelihood function, each of the one or more traits can be removed from the pool of selected traits S880. Moreover, upon removing each of the one or more traits from the pool of selected traits, the remaining, current pool of selected traits can be compared with each of the previous pools of selected traits S883. If, upon comparison at S883, the drug determining device determines that the current pool of selected traits is equal to a previous pool of selected traits, timeline model development can be stopped and the current timeline model can be applied to testing data S882. Alternatively, if the current pool of selected traits is different from any of the previous pools of selected traits, timeline model development returns to S875.

Figure 8B:
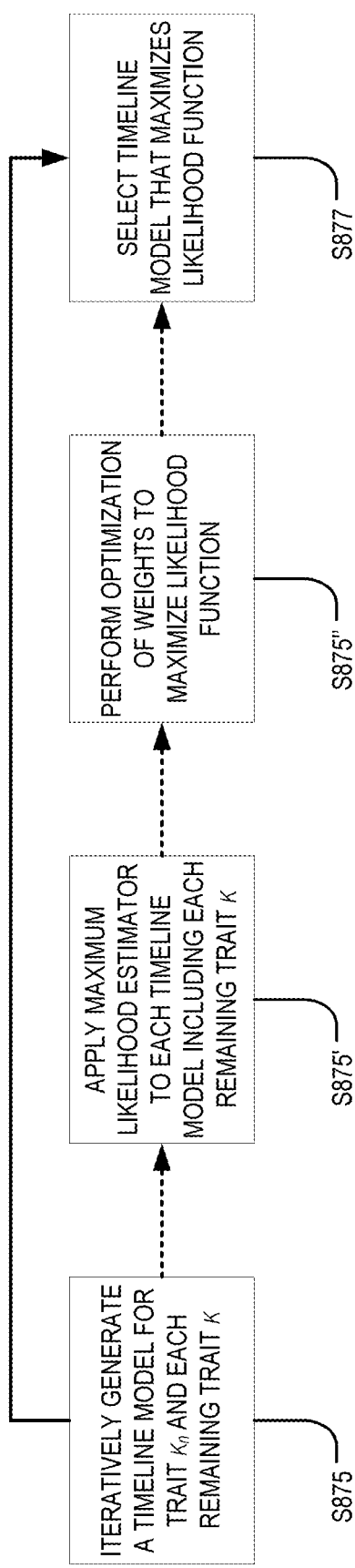
FIG. 8B is a low-level flowchart of an aspect of development of a timeline model of a drug, according to an exemplary embodiment of the present disclosure.

According to an embodiment, and in order to evaluate the predictive benefit of including traits within the timeline model, a maximum likelihood estimation can be used to determine the optimal set of coefficients $(w_1, w_2, \ldots, w_m)$ of Eq. (2). To this end, FIG. 8B is a low-level flowchart describing implementation of a maximum likelihood estimate in determining the timeline model described in FIG. 8A. According to an embodiment, FIG. 8B is described with respect to two or more selected traits, but it can be appreciated that a similar approach can be implemented with respect to a single selected trait, mutatis mutandis. Generally, following generation of a timeline model for each trait $k_n$ and each remaining trait k of set K S875, and prior to selection of a maximal timeline model S877, a maximum likelihood estimator can be applied to each generated timeline model to determine the predictive power of each timeline model. First, a maximum likelihood estimator can be applied to each timeline model S875'. Next, each weight w can be optimized in order to maximize each likelihood function S875". Having optimized each likelihood function, and considering each likelihood function associated with the timeline models, the timeline model that maximizes the likelihood function, and thus, the likelihood that an expected outcome happens, is selected for continued use within the development of the timeline model S877.

Specifically, according to an embodiment, a likelihood function can be determined for a training data set consisting of t drug programs. First, each drug program of t drug programs in the training data set can be sorted in ascending order of real transition times, or, the number of days after a starting date of a phase. When $t_1<t_2< \ldots <t_s$ denotes an s distinct, ordered event time, $d_i$ denotes the number of drug programs that have a transition time $t_i$ for $i=1, 2, 3, \ldots, s$, and $R_i$ denotes a set of all drug programs that have a transition time greater or equal to $t_i$, a likelihood function $L_i$, for each event time $t_i$, can be expressed as $$L_i = \prod_{j=1}^{d_i} \frac{H_j(t_i)}{\sum_{r \in R_i} H_r(t_i)}$$

where $H(t_i)$ is a hazard function as expressed in Eq. (2). Next, having defined a likelihood function for each event time of a training data set, individually, the combined likelihood function for the entire set can be expressed as $L=L_1*L_2*L_3* \ldots *L_s$ for $i=1, 2, 3, \ldots, s$. Having defined individual likelihood functions and a combined likelihood function S875', a numerical optimization method can be implemented to determine optimal weights to the maximum likelihood function S875". The numerical optimization method can be, among others, the Newton-Raphson method.

As applied in the present disclosure, the above-described approaches improve efficiency and overall speed in model development as implemented in the drug determining device. In addition to the proportional hazard model employed herein to estimate time to success, it can be appreciated that similar approaches within a class of survival models, or similar failure models, can be implemented to the same effect, as would be understood by one of ordinary skill in the art.

Figure 9:
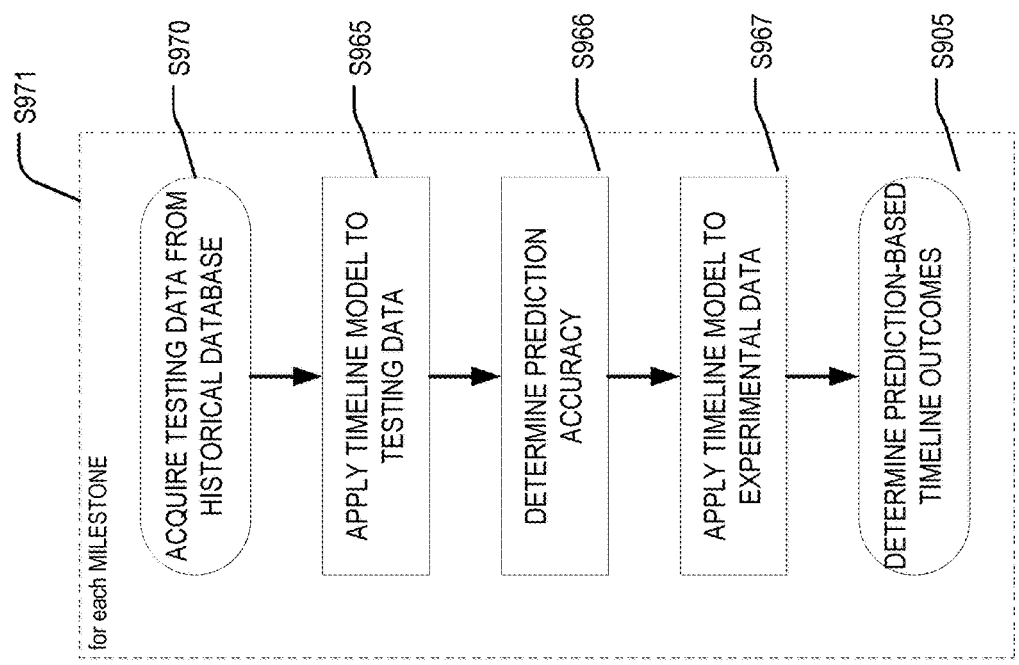
FIG. 9 is a high-level flowchart describing development of a timeline model of a drug, according to an exemplary embodiment of the present disclosure.

According to an embodiment, the training phase of timeline model development described in FIG. 8A as related to, for example, P1 to P2, can next be evaluated by application to testing data, as described in FIG. 9. Again, the testing phase of timeline model development can be performed on each of a plurality of milestones S971 selected during drug program selection. First, testing data acquired previously prior to the training phase can be acquired S970. Next, the timeline model developed during the training phase can be evaluated with the testing data S965. If the drug determining device determines that the timeline model does not provide an adequate level of prediction accuracy S966, additional regulatory data can be added to the training data such that the timeline model can be improved and the level of prediction accuracy can be increased. In an embodiment, the adequate level of prediction accuracy is a user-defined threshold based upon factors including, among others, the therapeutic indication. If, however, the drug determining device determines that the timeline model provides an adequate level of prediction accuracy S966, the timeline model can provide an estimated time to success S905 such that it can be utilized for determining the drug for manufacture. In an embodiment, the timeline model can be applied to additional experimental data, as requested by a user S967, in order to provide an estimated time to success S905 such that it can be utilized in determining the drug for manufacture.

The above-described development processes for models describing a probability of success and a time to success can be implemented by the drug determining device. FIG. 10 describes a predicted probability of approval for two drug programs 'pending regulatory approval', as indicated under 'in_status', the predicted probability being an intermediary step prior to determination of a drug for manufacture. As shown in FIG. 10, two drug programs comprising of a drug, or 'drug_id_n', a therapeutic indication, or 'disease_id', a country, or 'country', and a company, or 'company_id', are included. In an embodiment, the drug, the therapeutic indication, and the company remain constant across the two drug programs of interest. Further, qualitative regulatory traits including designation status, company size, and disease category are constant across the two drug programs. The country, however, in this case a particular market of development, is different between the two drug programs. It can be appreciated that while the United States and Europe are considered with the entity status 'country', these are merely representative of a plurality of other 'country' entries and, therefore, are non-limiting. This difference in country (or any other geographical descriptor) can result in a difference in predicted probability of success, observed in FIG. 10, as data from the historical database can include the effects of varying regulatory pathways faced in Europe as compared with the United States.

According to an embodiment, and with reference to FIG. 10, the drug determining device may further determine, in context of predicted time to success, to manufacture a drug for Europe with the understanding that this may improve the likelihood that the drug is able to reach patients more quickly.

According to an embodiment, and in addition to the model development process described above, the drug determining device can be further configured to implement a machine learning-based process for prediction of success probability and time to success. Moreover, as described below, the drug determining device can be further configured to provide alternative suggestions to a user in response to a user-defined input, via implementation of the machine learning-based process.

The machine learning-based process can employ a machine learning algorithm, trained via supervised learning, including, among others, support vector machines, neural networks, deep learning, feature selection, and learning classifier system. In an embodiment, the machine learning-based process can be, among others, a support vector machine. In order to generate a probabilistic output, the machine learning algorithm/process may be a support vector machine with Platt scaling. In an embodiment, the machine learning-based process can be a relevance vector machine. Generally, the machine learning algorithm/process may be a classification model, wherein a logistic regression model can be applied to the classifier's output such that a probabilistic output is rendered.

According to an embodiment, the machine learning-based process, and classifier, therein, can be trained on a training database, the training database comprising relevant regulatory data acquired from a historical database, as described above for FIG. 6A and FIG. 8A. More specifically, organized regulatory data can be relationally-arranged such that known sets of quantitative traits and qualitative traits are matched, or, in other words, a particular combination of entries of k traits of a specific drug program can be associated with a particular outcome of the specific drug program including, for example, a successful transition from P2 to P3. With the organized regulatory data arranged in this way, one or more machine learning-based methods, one for each development milestone, and corresponding to a success model and a timeline model, can be developed to predict a probability of a classification. In an embodiment, the classification can be a binary success-based classification. In an embodiment, the classification can be a timeline-based classification, wherein a trained classifier can classify a time to success within time-ordered bins including, for instance, 0 years to 2.5 years and 10 years to 12.5 years. The machine learning-based method described above, a relevance vector machine, in an example, can be implemented as described and as would be understood by one of ordinary skill in the art.

According to an embodiment, the classifier trained according to the above can be applied to a set of testing data to evaluate the accuracy of the trained classifier in predicting an expected outcome. In an example, the expected outcome may be a classification. In an example, the expected outcome may be a probability of an outcome. In an example, the expected outcome can be a predicted outcome of a corresponding developed model of FIG. 6A or FIG. 8. In each of the above, if the drug determining device determines that an output of the trained classifier is below a pre-determined accuracy threshold, additional training data may be added in order to improve, for example, the diversity of the training data and, thus, improve the accuracy of the output. In one embodiment, if the drug determining device determines that the output of the trained classifier is above the pre-determined accuracy threshold, the trained classifier may be applied to experimental data.

To this end, and according to an embodiment, a classifier can be trained to determine, based upon a specific combination of entries of m traits k, a probability of a successful transition from, for example, P3 to filing. The specific combination of entries of m traits k can include a combination of the traits described in FIG. 10. For instance, as non-limiting examples of two traits of m traits k, the type of drug compound can be a small molecule and the therapeutic area can be osteoarthritis. A combination of entries of m traits k, similar from that described above, can be submitted to the trained classifier which, in the case of the relevance vector machine, generates a probabilistic output indicating a chance of success based upon m traits k.

According to an embodiment, and in addition to the probabilistic output above, the drug determining device implementing the machine learning-based method/process can be further configured to perform an optimization to evaluate and propose adjustments to entries of m traits k. During optimization, similar combinations of m traits k can be evaluated to determine if an adjustment to the combination of m traits k can improve the probabilistic output. For example, in a user-defined combination of m traits k including an entry of 'public' for 'sponsor type', a concurrent machine learning based-method/process can be applied to a subsequent, drug determining device-generated combination of m traits k wherein the entry for 'sponsor type' can be 'private'. In an example, wherein a 'private' sponsor improves the probability of success, in generating a probabilistic output of the user-defined combination of m traits k, the machine learning-based method/process can simultaneously recommend the subsequent, drug determining device-generated combination of m traits k. In this way, the drug determining device can be configured to automatically identify similar combinations of m traits k, to evaluate each automatically identified similar combination, and to recommend an automatically-identified similar combination, if appropriate. In an embodiment, the drug determining device can be configured to adjust the combination of m traits k within a set of constraining parameters including, for example, a maximum number of adjusted traits k. In an embodiment, the drug determining device can be configured to recommend an automatically-identified similar combination if the probabilistic output may improve a chance for success.

Next, a hardware description of the drug determining device according to exemplary embodiments is described with reference to FIG. 11. The drug determining device may be a general-purpose computer or a particular, special-purpose machine. In one embodiment, the drug determining device becomes a particular, special-purpose machine when a processor (such as central processing unit (CPU) 1185) is programmed to the processes described herein.

Each of the functions of the described embodiments may be implemented by one or more processing circuits/circuitry. A processing circuit includes a programmed processor (for example, a processor or CPU 1185), as a processor includes circuitry. A processing circuit may also include devices such as an application specific integrated circuit (ASIC) and conventional circuit components arranged to perform the recited functions. In FIG. 11, the drug determining device includes the CPU 1185 which performs the processes described above. The process data and instructions may be stored in memory 1186. These processes and instructions may also be stored on a storage medium disk 1187 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the drug determining device communicates, such as a server or computer.

Further, the claimed advancements may be provided as a utility application, background daemon, or component of an operating system, or combination thereof, executing in conjunction with CPU 1185 and an operating system such as Microsoft Windows, UNIX, Solaris, LINUX, Apple MAC-OS and other systems known to those skilled in the art.

The hardware elements in order to achieve the drug determining device may be realized by various circuitry elements, known to those skilled in the art. For example, CPU 1185 may be a Xenon or Core processor from Intel of America or an Opteron processor from AMD of America, or may be other processor types that would be recognized by one of ordinary skill in the art. Alternatively, the CPU 1185 may be implemented on an FPGA, ASIC, PLD or using discrete logic circuits, as one of ordinary skill in the art would recognize. Further, CPU 1185 may be implemented as multiple processors cooperatively working in parallel to perform the instructions of the inventive processes described above.

Figure 11:
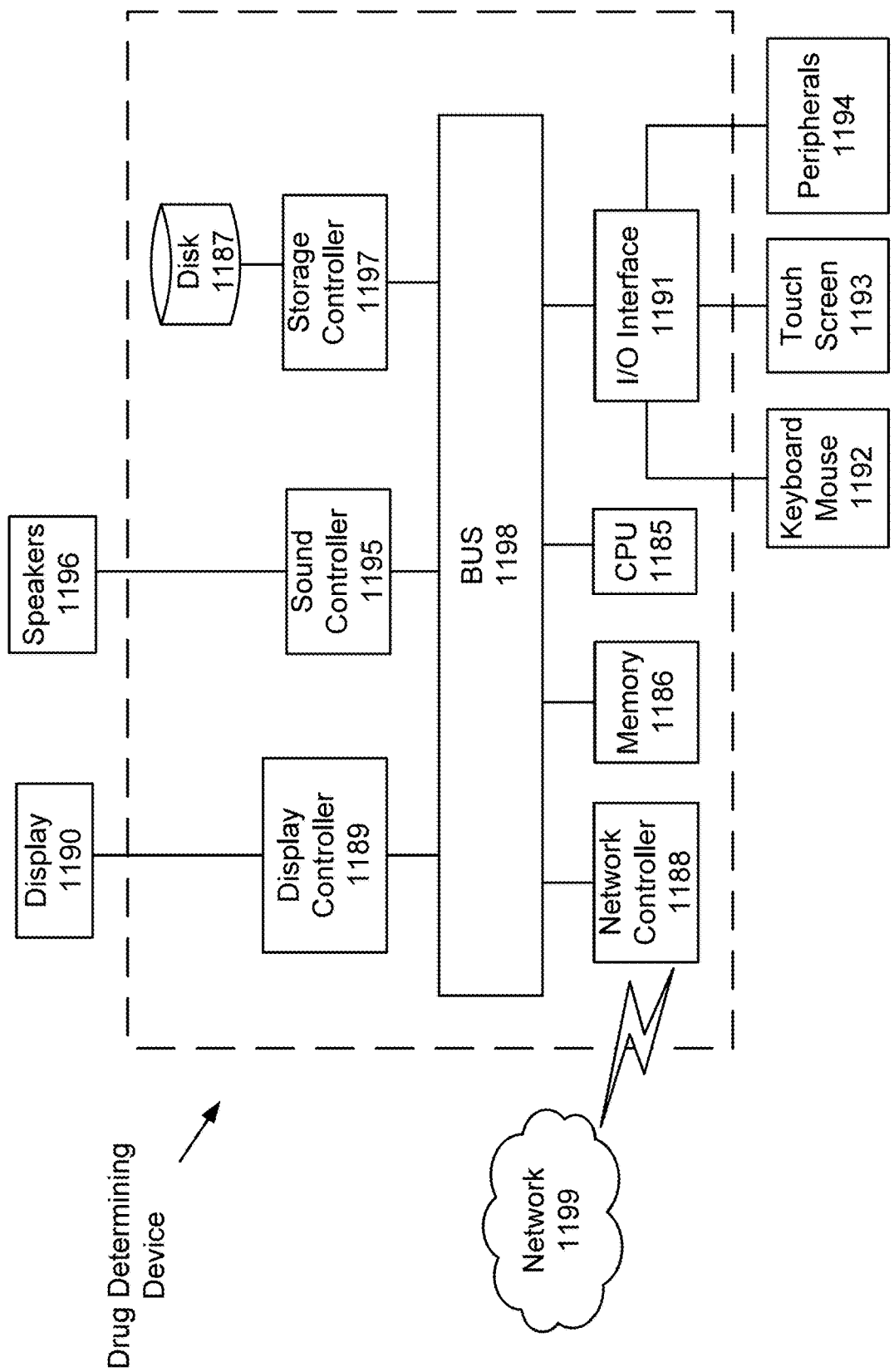
FIG. 11 is a hardware description of a drug determining device, according to an exemplary embodiment of the present disclosure.

The drug determining device in FIG. 11 also includes a network controller 1188, such as an Intel Ethernet PRO network interface card from Intel Corporation of America, for interfacing with network 1199. As can be appreciated, the network 1199 can be a public network, such as the Internet, or a private network such as an LAN or WAN network, or any combination thereof and can also include PSTN or ISDN sub-networks. The network 1199 can also be wired, such as an Ethernet network, or can be wireless such as a cellular network including EDGE, 3G and 4G wireless cellular systems. The wireless network can also be WiFi, Bluetooth, or any other wireless form of communication that is known.

The drug determining device further includes a display controller 1189, such as a NVIDIA GeForce GTX or Quadro graphics adaptor from NVIDIA Corporation of America for interfacing with display 1190, such as an LCD monitor. A general purpose I/O interface 1191 interfaces with a keyboard and/or mouse 1192 as well as a touch screen panel 1193 on or separate from display 1190. General purpose I/O interface also connects to a variety of peripherals 1194 including printers and scanners.

A sound controller 1195 is also provided in the drug determining device, such as Sound Blaster X-Fi Titanium from Creative, to interface with speakers/microphone 1196 thereby providing sounds and/or music.

The general purpose storage controller 1197 connects the storage medium disk 1187 with communication bus 1198, which may be an ISA, EISA, VESA, PCI, or similar, for interconnecting all of the components of the drug determining device. A description of the general features and functionality of the display 1190, keyboard and/or mouse 1192, as well as the display controller 1189, storage controller 1197, network controller 1188, sound controller 1195, and general purpose I/O interface 1191 is omitted herein for brevity as these features are known.

Embodiments of the present disclosure may also be as set forth in the following parentheticals.

(1) An apparatus for determining a drug for manufacture, the apparatus being communicably coupled via a network to a manufacturing device, the apparatus comprising processing circuitry configured to receive input data related to one or more drug programs, the input data related to the one or more drug programs describing a drug, a disease indication, and a geo location associated with a development of the drug, acquire data from a database, based upon the input data, wherein the acquired data comprises chronological data and qualitative data of one or more historical drug programs, the qualitative data being related to characteristics of a clinical trial, generate one or more models based upon the acquired data from the database, wherein each of the one or more models is related to a chronological event, the chronological event being one or more dates related to the clinical trial, determine, from the one or more models, one or more outputs related to the chronological event, select, based upon the determined one or more outputs, one of the one or more drug programs for manufacture, and transmit, to the manufacturing device via the network, manufacturing information related to the manufacture of the drug of the selected one of the one or more drug programs.

(2) The apparatus according to (1), wherein the processing circuitry selects one of the one or more drug programs for manufacture based upon a comparison of an output related to the chronological event of one of the one or more drug programs and a corresponding output related to the chronological event of a subsequent one of the one or more drug programs.

(3) The apparatus according to either (1) or (2), wherein the comparison is based upon a maximization of the output related to the chronological event, the output related to the chronological event being a success probability.

(4) The apparatus according to any of (1) to (3), wherein the processing circuitry is further configured to generate an initial model based upon an initial subset of one or more traits of the acquired data from the database generate a subsequent model based upon a subsequent subset of the one or more traits of the acquired data from the database, and select, based upon a comparison of the initial model and the subsequent model, one of either the initial model or the subsequent model, wherein the initial model or the subsequent model is selected to maximize a likelihood function, and wherein the selected model is maximized via a maximum likelihood estimator.

(5) The apparatus according to any of (1) to (4), wherein at least one of the one or more models is a success probability model, the success probability model being optimized via a maximum likelihood estimator.

(6) The apparatus according to any of (1) to (5), wherein at least one of the one or more models is a survival model, the survival model being a proportional hazard model.

(7) The apparatus according to any of (1) to (6), wherein the proportional hazard model is optimized via a maximum likelihood estimator.

(8) A method for determining a drug for manufacture, comprising receiving, by processing circuitry, input data related to one or more drug programs, the input data related to the one or more drug programs describing a drug, a disease indication, and a geo location associated with a development of the drug, acquiring, by the processing circuitry, data from a database, based upon the input data, wherein the acquired data comprises chronological data and qualitative data of one or more historical drug programs, the qualitative data being related to characteristics of a clinical trial, generating, by the processing circuitry, one or more models based upon the acquired data from the database, wherein each of the one or more models is related to a chronological event, the chronological event being one or more dates related to the clinical trial, determining, by the processing circuitry, from the one or more models, one or more outputs related to the chronological event, selecting, by the processing circuitry, based upon the determined one or more outputs, one of the one or more drug programs for manufacture, and transmitting, by the processing circuitry, to a manufacturing device via a network, manufacturing information related to the manufacture of the drug of the selected one of the one or more drug programs.

(9) The method according to (8), further comprising selecting, by the processing circuitry, one of the one or more drug programs for manufacture based upon a comparison of an output related to the chronological event of one of the one or more drug programs and a corresponding output related to the chronological event of a subsequent one of the one or more drug programs.

(10) The method according to either (8) or (9), wherein the comparison is based upon a maximization of the output related to the chronological event, the output related to the chronological event being a success probability.

(11) The method according to any of (8) to (10), further comprising generating, by the processing circuitry, an initial model based upon an initial subset of one or more traits of the acquired data from the database, generating, by the processing circuitry, a subsequent model based upon a subsequent subset of the one or more traits of the acquired data from the database, and selecting, by the processing circuitry, based upon a comparison of the initial model and the subsequent model, one of either the initial model or the subsequent model, wherein the initial model or the subsequent model is selected to maximize a likelihood function, and wherein the selected model is maximized via a maximum likelihood estimator.

(12) The method according to any of (8) to (11), wherein at least one of the one or more models is a success probability model, the success probability model being optimized via a maximum likelihood estimator.

(13) The method according to any of (8) to (12), wherein at least one of the one or more models is a survival model, the survival model being a proportional hazard model.

(14) The method according to any of (8) to (13), wherein the proportional hazard model is optimized via a maximum likelihood estimator.

(15) A non-transitory computer-readable storage medium storing computer-readable instructions that, when executed by a computer, cause the computer to perform a method of determining a drug for manufacture, comprising receiving input data related to one or more drug programs, the input data related to the one or more drug programs describing a drug, a disease indication, and a geo location associated with a development of the drug, acquiring data from a database, based upon the input data, wherein the acquired data comprises chronological data and qualitative data of one or more historical drug programs, the qualitative data being related to characteristics of a clinical trial, generating one or more models based upon the acquired data from the database, wherein each of the one or more models is related to a chronological event, the chronological event being one or more dates related to the clinical trial, determining, from the one or more models, one or more outputs related to the chronological event, selecting, based upon the determined one or more outputs, one of the one or more drug programs for manufacture, and transmitting, to a manufacturing device via a network, manufacturing information related to the manufacture of the drug of the selected one of the one or more drug programs.

(16) The non-transitory computer-readable storage medium according to (15), further comprising selecting one of the one or more drug programs for manufacture based upon a comparison of an output related to the chronological event of one of the one or more drug programs and a corresponding output related to the chronological event of a subsequent one of the one or more drug programs.

(17) The non-transitory computer-readable storage medium according to either (15) or (16), wherein the comparison is based upon a maximization of the output related to the chronological event, the output related to the chronological event being a success probability.

(18) The non-transitory computer-readable storage medium according to any of (15) to (17), further comprising generating an initial model based upon an initial subset of one or more traits of the acquired data from the database, generating a subsequent model based upon a subsequent subset of the one or more traits of the acquired data from the database, and selecting, based upon a comparison of the initial model and the subsequent model, one of either the initial model or the subsequent model, wherein the initial model or the subsequent model is selected to maximize a likelihood function, and wherein the selected model is maximized via a maximum likelihood estimator.

(19) The non-transitory computer-readable storage medium according to any of (15) to (18), wherein at least one of the one or more models is a success probability model, the success probability model being optimized via a maximum likelihood estimator.

(20) The non-transitory computer-readable storage medium according to any of (15) to (19), wherein at least one of the one or more models is a survival model, the survival model being optimized via a maximum likelihood estimator.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for determining a drug for manufacture, the apparatus being communicably coupled via a network to a manufacturing device, the apparatus comprising:
processing circuitry configured to
receive input data related to candidate drug programs, the input data describing, for each candidate drug program, a candidate drug, a disease indication, and a geo location associated with a development of the candidate drug,
acquire data from a database based upon the input data, wherein the acquired data comprises chronological data and qualitative data of historical drug programs related to each candidate drug program, the qualitative data describing characteristics of clinical trials associated with the historical drug programs,
generate, for each candidate drug program, at least one success model and at least one timeline model based on the acquired data from the database related to the historical drug programs, each of the at least one success model and the at least one timeline model being related to chronological events of the clinical trials associated with the historical drug programs, the chronological events being one or more milestone dates that define the clinical trials, wherein
each of the at least one success model is a logistic regression model including, as parameters thereof, a subset of characteristics of a respective clinical trial determined to positively affect a likelihood function defining the logistic regression model, and
each of the at least one timeline model is a proportional hazard model including, as parameters thereof, a subset of characteristics of a respective clinical trial determined to positively affect a likelihood function defining the proportional hazard model,
determine, from a composite of the at least one success model and a corresponding composite of the at least one timeline model for each candidate drug program, one or more outputs related to a corresponding chronological event for each of the candidate drug programs,
select, based upon the determined one or more outputs for each of the candidate drug programs, one of the candidate drug programs for manufacture, and
transmit, to the manufacturing device via the network, manufacturing information related to the manufacture of the candidate drug associated with the selected one of the candidate drug programs, the manufacturing device beginning the manufacture of the candidate drug upon receipt of the manufacturing information from the apparatus, wherein
the composite of the at least one success model predicts a probability that a respective candidate drug program will reach a particular milestone date of a respective clinical trial, and
the corresponding composite of the at least one timeline model predicts a time required for the respective candidate drug program to reach the particular milestone date of the respective clinical trial.

2. The apparatus according to claim 1, wherein the processing circuitry is configured to select the selected one of the candidate drug programs for manufacture by
comparing, as the one or more outputs for the candidate chug programs, a success probability that each candidate drug program will reach the particular milestone and a time required for each candidate drug program to reach the particular milestone.

3. The apparatus according to claim 2, wherein the processing circuitry is configured to select, based on the comparing and as the selected one of the candidate drug programs for manufacture, a candidate drug program that maximizes a success probability that a respective candidate drug program will reach a particular milestone.

4. The apparatus according to claim 1, wherein coefficients of the parameters of the logistic regression model are optimized via a maximum likelihood estimator.

5. The apparatus according to claim 1, wherein coefficients of the parameters of the proportional hazard model are optimized via a maximum likelihood estimator.

6. A method for determining a drug for manufacture, comprising:
receiving, by processing circuitry, input data related to candidate drug programs, the input data describing, for each candidate drug program, a candidate drug, a disease indication, and a geo location associated with a development of the candidate drug;

acquiring, by the processing circuitry, data from a database based upon the input data, wherein the acquired data comprises chronological data and qualitative data of historical drug programs related to each candidate drug program, the qualitative data describing characteristics of clinical trials associated with the historical drug programs;

generating, by the processing circuitry and for each candidate drug program, at least one success model and at least one timeline model based on the acquired data from the database related to the historical drug programs, each of the at least one success model and the at least one timeline model being related to chronological events of the clinical trials associated with the historical drug programs, the chronological events being one or more milestone dates that define the clinical trials, wherein
each of the at least one success model is a logistic regression model including, as parameters thereof, a subset of characteristics of a respective clinical trial determined to positively affect a likelihood function defining the logistic regression model, and
each of the at least one timeline model is a proportional hazard model including, as parameters thereof, a subset of characteristics of a respective clinical trial determined to positively affect a likelihood function defining the proportional hazard model;

determining, by the processing circuitry, from a composite of the at least one success model and a corresponding composite of the at least one timeline model for each candidate drug program, one or more outputs related to a corresponding chronological event for each of the candidate drug programs;

selecting, by the processing circuitry, based upon the determined one or more outputs for each of the candidate drug programs, one of the candidate drug programs for manufacture; and transmitting, by the processing circuitry, to a manufacturing device via a network, manufacturing information related to the manufacture of the candidate drug associated with the selected one of the candidate drug programs, the manufacturing device beginning the manufacture of the candidate drug upon receipt of the manufacturing information, wherein the composite of the at least one success model predicts a probability that a respective candidate drug program will reach a particular milestone date of a respective clinical trial, and the corresponding composite of the at least one timeline model predicts a time required for the respective candidate drug program to reach the particular milestone date of the respective clinical trial.

7. The method according to claim 6, wherein the selecting, by the processing circuitry, further comprises
comparing, as the one or more outputs for the candidate drug programs, a success probability that each candidate drug program will reach the particular milestone and a time required for each candidate drug program to reach the particular milestone.

8. The method according to claim 7, wherein the selecting selects, based on the comparing as the selected one of the candidate drug programs for manufacture, a candidate drug program that maximizes a success probability that a respective candidate drug program will reach a particular milestone.

9. The method according to claim 6, wherein coefficients of the parameters of the logistic regression model are optimized via a maximum likelihood estimator.

10. The method according to claim 6, wherein coefficients of the parameters of the proportional hazard model are optimized via a maximum likelihood estimator.

11. A non-transitory computer-readable storage medium storing computer-readable instructions that, when executed by a computer, cause the computer to perform a method of determining a drug for manufacture, comprising:
receiving input data related to candidate drug programs, the input data describing a candidate drug, a disease indication, and a geo location associated with a development of the candidate drug;
acquiring data from a database based upon the input data, wherein the acquired data comprises chronological data and qualitative data of historical drug programs related to each candidate drug program, the qualitative data describing characteristics of clinical trials associated with the historical drug programs;
generating, for each candidate drug program, at least one success model and at least one timeline model based on the acquired data from the database related to the historical drug programs, each of the at least one success model and the at least one timeline model being related to chronological events of the clinical trials associated with the historical drug programs, the chronological events being one or more milestone dates that define the clinical trials, wherein
each of the at least one success model is a logistic regression model including, as parameters thereof, a subset of characteristics of a respective clinical trial determined to positively affect a likelihood function defining the logistic regression model, and
each of the at least one timeline model is a proportional hazard model including, as parameters thereof, a subset of characteristics of a respective clinical trial determined to positively affect a likelihood function defining the proportional hazard model;
determining, from a composite of the at least one success model and a corresponding composite of the at least one timeline model for each candidate drug program, one or more outputs related to a chronological event for each of the candidate drug programs;
selecting, based upon the determined one or more outputs for each of the candidate drug programs, one of the candidate drug programs for manufacture; and
transmitting, to a manufacturing device via a network, manufacturing information related to the manufacture of the candidate drug associated with the selected one of the candidate drug programs, the manufacturing device beginning the manufacture of the candidate drug upon receipt of the manufacturing information, wherein
the composite of the at least one success model predicts a probability that a respective candidate drug program will reach a particular milestone date of a respective clinical trial, and
the corresponding composite of the at least one timeline model predicts a time required for the respective candidate drug program to reach the particular milestone date of the respective clinical trial.

12. The non-transitory computer-readable storage medium according to claim 11, wherein the selecting further comprises comparing, as the one or more outputs for the candidate chug programs, a success probability that each candidate drug program will reach the particular milestone and a time required for each candidate drug program to reach the particular milestone.

13. The non-transitory computer-readable storage medium according to claim 12, wherein the selecting selects, based on the comparing as the selected one of the candidate drug programs for manufacture, a candidate drug program that maximizes a success probability that a respective candidate drug program will reach a particular milestone.

14. The non-transitory computer-readable storage medium according to claim 11, wherein coefficients of the parameters of the logistic regression model are optimized via a maximum likelihood estimator.

15. The non-transitory computer-readable storage medium according to claim 11, wherein coefficients of the parameters of the proportional hazard model are optimized via a maximum likelihood estimator.

* * * * *